US006818221B2

(12) United States Patent
Pulendran et al.

(10) Patent No.: US 6,818,221 B2
(45) Date of Patent: Nov. 16, 2004

(54) ADJUVANTS AND PROCESSES TO INDUCE A SPECIFIC TYPE OF IMMUNE RESPONSE

(75) Inventors: Bali Pulendran, Atlanta, GA (US); Jacques F. Banchereau, Dallas, TX (US); Christopher W. Cutler, Stony Brook, NY (US)

(73) Assignee: Baylor Research Institute, Dallas, TX (US)

(*) Notice: Subject to any disclaimer, the term of this patent is extended or adjusted under 35 U.S.C. 154(b) by 0 days.

(21) Appl. No.: 10/311,123

(22) PCT Filed: Jun. 18, 2001

(86) PCT No.: PCT/US01/19411

§ 371 (c)(1),
(2), (4) Date: Jun. 6, 2003

(87) PCT Pub. No.: WO01/97838

PCT Pub. Date: Dec. 27, 2001

(65) Prior Publication Data

US 2004/0082538 A1 Apr. 29, 2004

Related U.S. Application Data

(60) Provisional application No. 60/212,182, filed on Jun. 16, 2000.

(51) Int. Cl.[7] .......................... A61K 39/02; A61K 45/00
(52) U.S. Cl. ................................. 424/234.1; 424/282.1
(58) Field of Search ........................... 424/234.1, 282.1

(56) References Cited

U.S. PATENT DOCUMENTS 6,129,917 A * 10/2000 Potempa et al. .......... 424/184.1
6,528,038 B1 * 3/2003 Reynolds et al. ............ 424/9.2

OTHER PUBLICATIONS

Reife et al., Infection and Immunity (1995), 63(12), 4686–94. Abstract Only.*
Aoyagi, et al. 1995. "Interleukin 4 (IL–4) and IL–6–producing memory T–cells in peripheral blood and gingival tissues in periodontitis patients with high serum antibody titers to *Porphyromonas gingivalis*," *Oral Microbiol Immunol* 10:304–310.
Barnden, M.J., et al. 1998. "Defective TCR expression in transgenic mice constructed using cDNA–based alpha–and beta–chain genes under the control of heterologous regulatory elements," *Immunol Cell Biol* 76:34–40.
Cutler, C.W., et al. 1996. "Hemin–induced modifications of the antigenicity and hemin–binding capacity of *Porphyromonas gingivalis* lipopolysaccharide," *Infect Immun* 64:2282–2287.
Hogquist, K.A., et al. 1994. "T cell receptor antagonist peptides induce positive selection," *Cell* 76:17–27.
Johnson, A.G., et al. 1987. "Characterization of a nontoxic monophosphoryl lipid A," *Rev Infectious Diseases* 9 (Suppl 5):S512–S516.

Kearney, E.R., et al. 1995, "Antigen–dependent clonal expansion of a trace population of antigen–specific CD4+ T cells in vivo is dependent on CD28 costimulation and inhibited by CTLA–4," *J Immunol* 155:1032–1036.
Khoruts, A., et al. 1998. "A natural immunological adjuvant enhances T cell clonal expansion through a CD28–dependent, interleukin (IL)–2–independent mechanism," *J Exp Med* 187:225–236.
Maldonado–Lopez, R., et al. 1999. "$CD8\alpha^+$ and $CD8\alpha^-$ subclasses of dendritic cells direct the development of distinct T helper cells in vivo," *J Exp Med* 189:587–592.
Martin, S. and M.J. Bevan. 1997. "Antigen–specific and nonspecific deletion of immature cortical thymocytes caused by antigen injection," *Eur J Immunol* 27:2726–2736.
Pulendran, B., et al. 1997 "Developmental pathways of dendritic cells in vivo: distinct function, phenotype, and localization of dendritic cell subsets in FLT3 ligand–treated mice," *J Immunol* 159:2222–2231.
Pulendran, B., et al. 1999. "Distinct dendritic cell subsets differentially regulate the class of immune response in vivo," *Proc Natl Acad Sci USA* 96:1036–1041.
Pulendran, B., et al. 2001. "Modulating the immune response with dendritic cells and their growth factors," *Trends in Immunology* 22(1):41–47.
Qureshi, S.T., et al. 1999. "Endotoxin–tolerant mice have mutations in Toll–like receptor 4 (*Tlr4*)," *J Exp Med* 189:615–625.
Reis e Sousa, C. and R.N. Germain. 1999. "Analysis of adjuvant function by direct visualization of antigen presentation in vivo: endotoxin promotes accumulation of antigen–bearing dendritic cells in the T cell areas of lymphoid tissue," *J Immunol* 162:6552–6561.
Rietschel, E.T., et al. 1994. "Bacterial endotoxin: molecular relationships of structure to activity and function," *FASEB Journal* 8:217–225.
Rissoan, M.C., et al. 1999. "Reciprocal control of T helper cell and dendritic cell differentiation," *Science* 283:1183–1186.
Shortman, K., et al. 1998. "The linkage between T–cell and dendritic cell development in the mouse thymus," *Immunolog Rev* 165:39–46.

(List continued on next page.)

Primary Examiner—Raymond J. Henley, III
(74) Attorney, Agent, or Firm—Sidley Austin Brown & Wood LLP

(57) ABSTRACT

*Porphyromanas gingivalis* LPS elicits a Th2 immune response. *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, or mimetics thereof, can be used as adjuvants to elicit a Th2 immune response, increase the efficacy of vaccinations in infectious diseases, decrease the severity of autoimmune responses, boost the Th2 immune response when needed in combination with the Th1 immune response, facilitate the industrial production of antibodies when used in animals, and study the Th2 immune response in laboratory animal research.

22 Claims, 18 Drawing Sheets

OTHER PUBLICATIONS

Singh, M., et al. 1998. "A comparison of biodegradable microparticles and MF59 as systemic adjuvants for recombinant gD from HSV–2," *Vaccine* 16:1822–1827.

Tanamoto, K., et al. 1997. "The lipid A moiety of *Porphyromonas gingivalis* lipopolysaccharide specifically mediates the activation of C3H/HeJ mice," *J Immunol* 158:4430–4436.

Valensi, et al. 1994. "Systemic cytokine profiles in BALB/c mice immunized with trivalent influenza vaccine containing MF59 oil emulsion and other advanced adjuvants," *J Immunol* 153:4029–4039.

Westphal, O., and K. Jann. 1965. "Bacterial lipopolysaccharides. Extraction with phenol–water and further applications of the procedure," *Methods Carbohydrate Chem* (R.L. Whistler, ed), Academic Press, New York; vol. 5:83–91.

Yamamoto, et al. 1997. "A nontoxic mutant of cholera toxin elicits Th–2–type responses for enhanced mucosal immunity," *Proc Natl Acad Sci USA* 94:5267–5272.

Morel, PA and Oriss, TB 1998. "Crossregulation between Th1 and Th2 cells," Crit Rev Immunol 18: 275–303.

* cited by examiner

- control
- OVA
- OVA+E.coli LPS
- OVA+P.gingivalis LPS

Intraperitoneal Injection

Subcutaneous Injection

- ◆ OVA
- ■ OVA+E.Coli
- ▲ OVA+P.gingivalis

Intraperitoneal Injection
- ◆ OVA
- ■ OVA+E.Coli
- ▲ OVA+P.gingivalis

Subcutaneous Injection

Intraperitoneal Injection

Subcutaneous Injection

◆ OVA
■ OVA+E.Coli
▲ OVA+P.gingivalis

IL-2

IFNγ

IL-10

IL-5

Intraperitoneal
Injection

◆ OVA
■ OVA+E.Coli
▲ OVA+P.gingivalis

IL-2

IFN γ

IL-10

IL-5

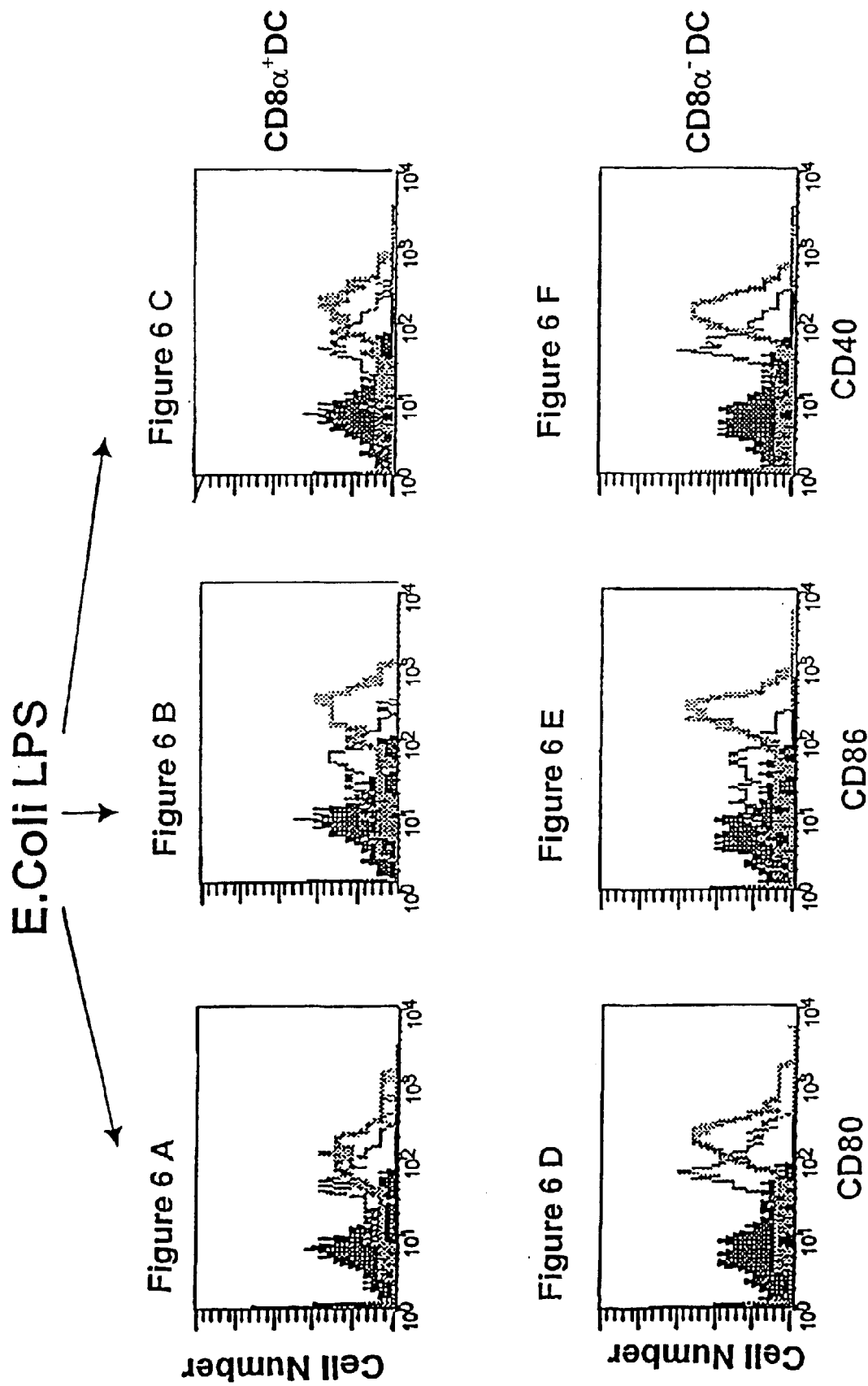

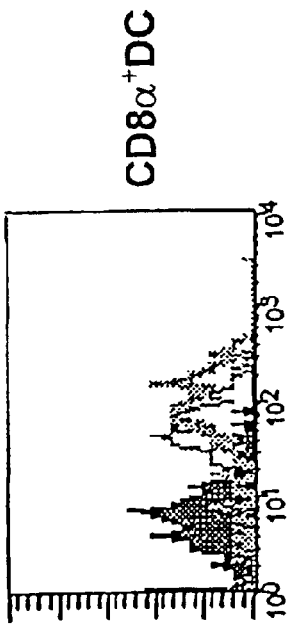
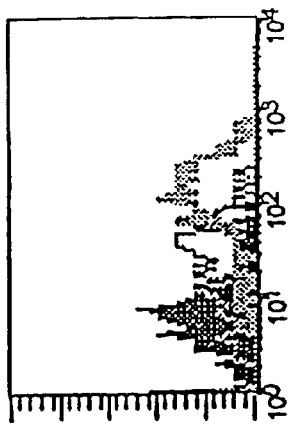
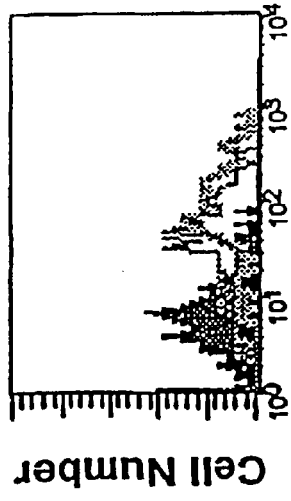
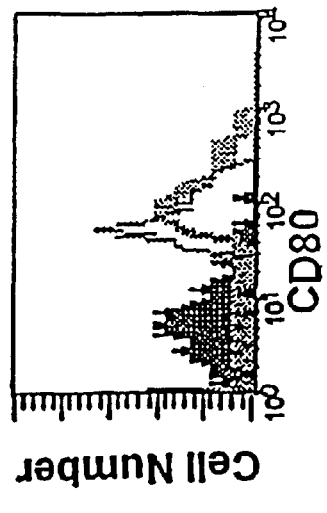

48 hr E.Coli LPS IL-6

48 hr P.gingivalis LPS IL-6

SEQUENCE LISTING

```
<160> NUMBER OF SEQ ID NOS: 1

<210> SEQ ID NO 1
<211> LENGTH: 8
<212> TYPE: PRT
<213> ORGANISM: chicken
<220> FEATURE:
<221> NAME/KEY: PEPTIDE
<222> LOCATION: (1)..(8)

<400> SEQUENCE: 1

Ser Ile Ile Asn Phe Glu Lys Leu
1               5
```

ADJUVANTS AND PROCESSES TO INDUCE A SPECIFIC TYPE OF IMMUNE RESPONSE

CROSS-REFERENCE TO RELATED APPLICATION

This application is the National Stage of International Application No. PCT/US01/19411, filed Jun. 18, 2001, which claims the benefit of U.S. Provisional Patent Application Ser. No. 60/212,182, filed Jun. 16, 2000.

TECHNICAL FIELD

The present invention relates to the field of using adjuvants to promote a specific type of immunological response.

BACKGROUND

The immune system has evolved two different types of adaptive immunity, each specialized for the elimination of a particular class of pathogens. In response to intracellular microbes, CD4+ T-helper (Th) cells differentiate into Th1 cells, which produce interferon γ (IFNγ) and interleukin (IL)-1, which, in turn, enhance cell-mediated immunity and inhibit the humoral immune responses. In contrast, helminths induce differentiation of CD4+ T-helper (Th) cells into Th2 cells, which produce cytokines (principally IL-4, IL-5, and IL-10) to induce immunoglobulin E (IgE) and eosinophil-mediated destruction of pathogens. The Th2 immune response inhibits cell-mediated immunity and enhances humoral immunity. The mechanism by which a given pathogen induces a Th1 or Th2 type of immune response is unknown.

Distinct subsets of dendritic cells (DCs) differentially induce Th1 and Th2 immune responses. In mice, the putative lymphoid-related CD8α+ DCs in spleens induce Th1 immune responses (Shortman, K. D., et al. 1998. "The linkage between T-cell and dendritic cell development in the mouse thymus," *Immune Rev* 165:39–46). In contrast, Th2 immune responses are induced by the CD8α-myeloid DCs (Maldonado-Lopez, R., et al. 1999. "CD8α+ and CD8α− subclasses of dendritic cells direct the development of distinct T helper cells in vivo," *J Exp Med* 189:587–592; Pulendran, B., et al. 1999. "Distinct dendritic cell subsets differentially regulate the class of immune response in vivo," *Proc Natl Acad Sci USA* 96:1036–1041; Rissoan, M. C., et al. 1999. "Reciprocal control of T helper cell and dendritic cell differentiation," *Science* 283:1183–1186). Different patterns of immunity can be elicited by activating distinct DC subsets.

*Escherichia coli* lipopolysaccharide (LPS) is reported to signal through the Toll-like receptor 4 (TLR4) complex (Qureshi, S. T., et al. 1999. "Endotoxin-tolerant mice have mutations in Toll-like receptor 4 (Tlr4)," *J Exp Med* 189:615–625; published erratum appears in *J Exp Med* 189:1518) and promote a Th1 immune response in vivo (Khoruts, A., A., et al. 1998. "A natural immunological adjuvant enhances T cell clonal expansion through a CD28-dependent, interleukin (IL)-2-independent mechanism," *J Exp Med* 187:225–236). In contrast, *Porphyromonas gingivalis* LPS is reported to signal through a TLR4-independent mechanism (Tanamoto, K., S., et al. 1997. "The lipid A moiety of *Porphyromonas gingivalis* lipopolysaccharide specifically mediates the activation of C3H/HeJ mice," *J Immunol* 158:4430–4436). It has now been found that although the LPS from these two different bacterial sources induce potent clonal expansion of antigen-specific CD4+ and CD8+ T cells in mice, they elicit strikingly different T cell cytokine profiles through differential cytokine expression by the CD8α+ and CD8α− DCs.

Although the use of adjuvants with antigen delivery to boost immunity is well known in the prior art, the adjuvants of the prior art reportedly elicit only a Th1 immune response. Currently, there is no known way to elicit a selective Th2 immune response with an adjuvant. A means of eliciting Th2 immune responses using *P. gingivalis* LPS has now been found, the application of the same to prevent and treat disease in humans and animals (mammals), increase antibody production in industrial practice, and to provide a method for studying the immune response in laboratory animals are presented herein.

BRIEF DESCRIPTION OF THE DRAWINGS

FIG. 2A depicts flow cytometry profiles from Day 4 of the response in the popliteal lymph nodes (subcutaneous route), from a representative experiment. FIGS. 2B and 2C depict the percentage expansion of OVA-specific CD4+ T cells (Thy1.2+, CD4+) in the draining lymph nodes and the spleens, respectively, at Day 4. Both *E. coli* LPS and *P. gingivalis* LPS significantly enhanced the clonal expansion, regardless of the route of injection. FIGS. 2D and 2E depict the absolute numbers of Thy 1.2+ CD4+ cells per popliteal lymph node or per spleen, respectively, at Day 4. FIGS. 2F and 2G depict in vitro restimulation of OVA-specific T cells expanded in vivo, by footpad injections or intraperitoneal injections, respectively. Four days after priming, single cell suspensions from the draining popliteal lymph nodes (FIG. 2F) or spleens (FIG. 2G) were restimulated with varying concentrations of OVA for 72 hours, and pulsed with [$^3$H] for 12 hours. Injections of *E. coli* LPS alone, or *P. gingivalis* LPS alone did not result in significant clonal expansion or in vitro proliferation. The data presented in FIGS. 2A–2G are representative of ten independent experiments.

FIG. 4A depicts flow cytometry profiles from Day 4 of the response in the popliteal lymph nodes from a representative experiment. FIGS. 4B and 4C depict the percentage expansion of OVA-specific CD8+ T cells (CD8+ Thy1.2+) in the draining lymph nodes and the spleens, respectively, at Day 4. Both E. coli LPS and P. gingivalis LPS significantly enhance the clonal expansion, regardless of the route of injection. FIGS. 4D and 4E depict the absolute numbers of OVA-specific CD8+ T cells per popliteal lymph node or per spleen, respectively, at Day 4. FIGS. 4F and 4G depict in vitro restimulation of OVA-specific CD8+ T cells expanded in vivo, by footpad injections or intraperitoneal injections, respectively. Four days after priming, single cell suspensions from the draining popliteal lymph nodes (FIG. 4F) or spleens (FIG. 4G) were restimulated with varying concentrations of OVA for 72 hours, and pulsed with [$^3$H] for 12 hours. Injections of E. coli LPS alone or P. gingivalis LPS alone did not result in significant clonal expansion, or in vitro proliferation (data not shown). The data presented in FIGS. 4A–4G are representative of three independent experiments.

FIGS. 6A–6L depict both E. coli LPS and P. gingivalis LPS activating CD8α+ and CD8α− DC subsets in vivo. C57BL/6 mice were injected with PBS (light histograms), or with E. coli LPS or P. gingivalis LPS (heavy, open histograms), either intravenously or intraperitoneally, and 6 hours later, the expression of CD80 (FIGS. 6A, 6D, 6G, and 6J), CD86 (FIGS. 6B, 6E, 6H, and 6K), and CD40 (FIGS. 6C, 6F, 6I, and 6L) assessed on gated, splenic CD11c+ CD8α+ and CD11c+ CD8α− DC subsets, by flow cytometry. Isotype controls are filled histograms. The data presented in FIGS. 6A–6L are representative of three experiments.

SUMMARY OF THE INVENTION

Figure 1:
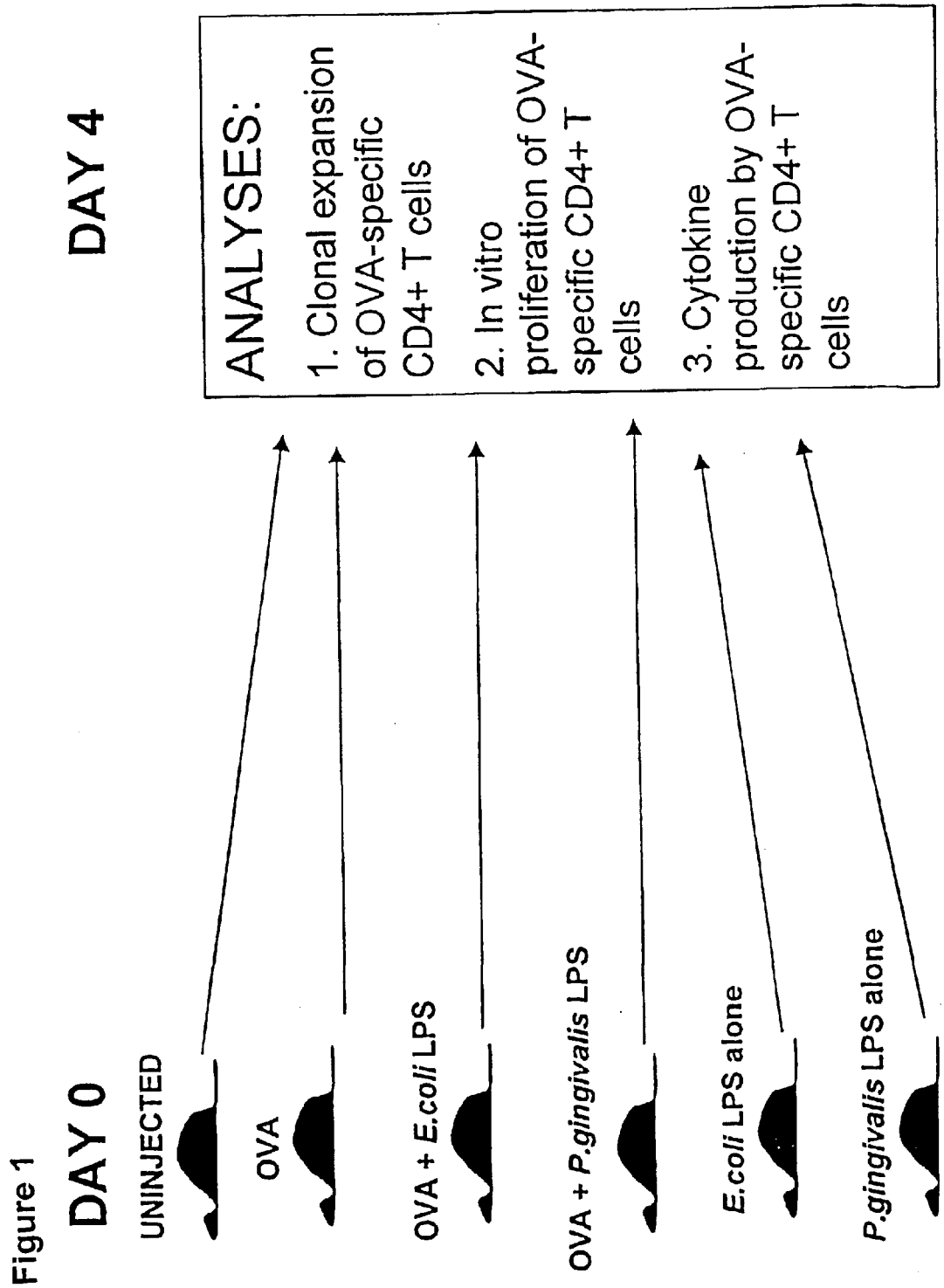
FIG. 1 depicts the experimental design utilized herein. B6.PL.THY1$^a$ (B6.PL) mice or C57BL/6 mice reconstituted with OT-2 cells were injected with either soluble OVA, soluble OVA+*E. coli* LPS, soluble OVA+*P. gingivalis* LPS, *E. coli* LPS alone, or *P. gingivalis* LPS alone intraperitoneally or in the footpad. Four days later, the spleens (intraperitoneal route) or draining lymph nodes (footpad route) were removed for phenotypic and functional analyses, including clonal expansion of OVA-specific CD4+ T cells, in vitro proliferation of OVA-specific CD4+ T cells and cytokine production by the OVA-specific CD4+ T cells.

In one aspect, the invention is a use of an effective amount of adjuvant comprising at least one isolated lipid moiety selected from the group consisting of P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, and mimetics thereof, for the preparation of a pharmaceutical composition for eliciting a Th2 response in a mammal. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, and mimetics thereof, for the preparation of a pharmaceutical composition for enhancing the immunogenicity of a vaccine in a mammal. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, and mimetics thereof, for the preparation of a pharmaceutical composition for modulating immunocompetence of a mammal. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof, for the preparation of a pharmaceutical composition for enhancing antibody harvest in a laboratory animal through elicited Th2 immune response. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof, for the preparation of a pharmaceutical composition for treating an autoimmune disease in a mammal. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof, for the preparation of a pharmaceutical composition for treating an infectious disease in a mammal. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof, for the preparation of a pharmaceutical composition for modulating the Th2 immune response in a laboratory animal. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof, for the preparation of a pharmaceutical composition for stimulating IL-5 production in a mammal. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof, for the preparation of a pharmaceutical composition for stimulating IL-13 production in a mammal. In one embodiment, the pharmaceutical composition further comprises disease-specific antigens. In another embodiment, the pharmaceutical composition further comprises a co-adjuvant which elicits a Th1 immune response.

In another aspect, the invention is a use of an effective amount of an adjuvant comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof, for the preparation of a pharmaceutical composition for dampening IFNγ production in a mammal. In one embodiment, the pharmaceutical composition further comprises disease-specific antigens. In another embodiment, the pharmaceutical composition further comprises a co-adjuvant which elicits a Th1 immune response.

In another aspect, the invention is a pharmaceutical composition comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the pharmaceutical composition further comprises disease-specific antigens. In another embodiment, the pharmaceutical composition further comprises a co-adjuvant which elicits a Th1 immune response.

In another aspect, the invention is a method of eliciting a Th2 immune response in a mammal comprising administering an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method of enhancing the immunogenicity of a vaccine in a mammal comprising co-administering disease-specific antigens and an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method of modulating immunocompetence of a mammal comprising administering an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method of enhancing antibody harvest in a laboratory animal through elicited Th2 immune response comprising administering to the animal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method for treating autoimmune disease in a mammal comprising administering to the mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method for treating an infectious disease in a mammal comprising administering to the mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method of modulating the Th2 immune response in a laboratory animal comprising administering to the mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method of stimulating IL-5 production in a mammal comprising administering an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method of stimulating IL-13 production in a mammal comprising administering an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

In another aspect, the invention is a method of dampening IFNγ production in a mammal comprising administering an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof. In one embodiment, the method further comprises co-administering to the mammal disease-specific antigens. In another embodiment, the method further comprises co-administering to the mammal a co-adjuvant which elicits a Th1 immune response. The adjuvant, disease-specific antigens and, optionally, the co-adjuvant can be administered concurrently or sequentially.

DETAILED DESCRIPTION OF THE INVENTION

According to the present invention, *P. gingivalis* lipopolysaccharide (LPS) can be extracted from any isolated strain of *Porphyromonas gingivalis*. For example, *P. gingivalis* 33277, *P. gingivalis* 49417, and *P. gingivalis* 53978 from the American Type Culture Collection (Manassas, Va.) can be utilized. A clinical *P. gingivalis* isolate is another acceptable source for LPS extraction.

Although *P. gingivalis* LPS may be toxic from de novo preparations, it can be detoxified with existing technology without compromising its adjuvant activity (Rietschel, E. T., et al. 1994. "Bacterial endotoxin: molecular relationships of structure to activity and function," *FASEB Journal* 8:217–825; Johnson, A. G., et al. 1987. "Characterization of a nontoxic monophosphoryl lipid A," *Rev Infectious Diseases* 9 (Suppl 5):S512–S516). *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof can be used to induce a Th2 immune response in humans and animals for clinical benefit, experimental purposes, or industrial applications. A compound "derivative" is structurally similar and possesses similar immunologic properties to the compound itself and may be naturally occurring or synthetic.

In one aspect, the invention disclosed herein is the elicitation of a Th2 immune response through the administration of an adjuvant comprising one or more of the following: *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, or mimetics thereof. According to the instant invention, *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof, used singly or in any combination, are considered suitable for use as an adjuvant to produce a Th2 immune response in a human or animal. Moreover, *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, or a mimetic thereof can be used in combination with other adjuvants known in the art to modulate and induce immune responses in humans and animals.

The selective elicitation of the Th2 immune response is highly desirable for treatment or prophylactic vaccination of humans or animals against various autoimmune diseases and graft-versus-host disease. Many autoimmune diseases are characterized by pathogenic Th1 immune responses. Currently, there are intensive efforts to discover adjuvants that can redirect a pathogenic Th1 immune response towards a benign Th2 immune response. Activating a Th2 immune response in a human or animal suffering from an autoimmune disease may decrease the pathogenic Th1 immune response, thereby decreasing the debilitating inflammation characteristic of such diseases. According to the instant invention, this effect of activating a Th2 immune response in a human or animal can be achieved through administration of a therapeutically effective composition comprising *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof by methods well known in the art (Pulendran, B., et al. 2001. "Modulating the immune response with dendritic cells and their growth factors," *Trends in Immunology* 22(1):41–47).

Therapeutic immunity against many tumors or infectious diseases or in transplantation requires Th2 immune responses. According to the instant invention, these diseases can be treated by administration of an adjuvant comprising *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof to induce a Th2 immune response.

Furthermore, therapeutic immunity against many tumors or infectious diseases often require both Th1 and Th2 immune responses simultaneously. According to the instant invention, *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof can be co-administered concurrently or sequentially with an adjuvant causing a Th1 immune response when a mixed response is required in the prevention or cure of diseases affecting humans or animals. This effect can be achieved through the introduction of a therapeutically effective amount of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof by methods well known in the art (Pulendran, B., et al. 2001. "Modulating the immune response with dendritic cells and their growth factors," *Trends in Immunology* 22(1):4147).

Methods for administering an adjuvant for the purpose of modulating an immune response are well known in the art (Pulendran, B., et al. 2001. "Modulating the immune response with dendritic cells and their growth factors," *Trends in Immunology* 22(1):41–47). To elicit a Th2 immune response, an adjuvant comprising *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof is preferably administered intravenously, intra-arterially, intra-muscularly, intra-dermally, and local (e.g., intra-tumoral or at the vicinity of a tumor site). Regardless of administration route, *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof can be administered with or without additional adjuvants and antigens. An effective amount of *P. gingivalis* LPS, detoxified *P. gingivalis* LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof will elicit a Th2 immune response in a human or animal. A suitable pharmaceutical carrier or diluent for administering an effective amount of P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof maintains the solubility of the compound. Formulating an effective amount of P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof to elicit a Th2 immune response in a human or animal for oral administration is also contemplated.

In another aspect, the instant invention is a method of enhancing the immunogenicity of a vaccine by administering an adjuvant comprising one or more of the following: P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, or mimetics thereof. The adjuvant of the instant invention can be administered concurrently or sequentially with a vaccine to enhance immunity by eliciting a Th2 immune response. Sequential administration indicates that the adjuvant and vaccine may be injected separately, in any order. Preferred administration routes include intravenous, intra-arterial, intramuscular, intra-dermal, and local (e.g., intra-tumoral or at the vicinity of a tumor site). Methods for co-administering an adjuvant with a vaccine to increase immunoreactivity are well known in the art (Pulendran, B., et al. 2001. "Modulating the immune response with dendritic cells and their growth factors," *Trends in Immunology* 22(1):41–47).

In addition to treating diseases, the instant invention includes use of adjuvants comprising P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof as research tools to study the immune system in laboratory animals. P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof can also be used in conjunction with an antigen for enhancing the production and harvest of antibodies in animals by methods well known in the art.

The following examples of the instant invention are illustrative of some of the applications of the invention but are not meant to be limiting in any way. Any use of P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof to induce a Th2 immune response is herein contemplated by the instant invention. It will be appreciated by those skilled in the art that the following methods and materials are exemplary and that other methods and materials may be employed to achieve the same result.

Mice

OT-2 TCR transgenic mice (strain 426-6), generated by Dr. W. Heath (Walter & Eliza Hall Institute, Melbourne, Australia) and Dr. F. Carbone (Monash University, Melbourne, Australia) were obtained from Dr. J. Kapp (Emory University, Atlanta). OT-1 TCR transgenic mice were purchased from Jackson Laboratory (Bar Harbor, Me.). C57BL/6 mice, B6.PL.THY1$^a$ (B6.PL) mice, and C3H/HeJ mice were purchased from Jackson Laboratory (Bar Harbor, Me.). C3H/HeN mice were purchased from Harlan Sprague Dawley (Indianapolis, Ind.). All mice were kept in microisolator cages in a specific-pathogen free facility. For adoptive transfers, age matched, male C57BL/6 or B6.PL.THY1$^a$ recipients were given $2.5 \times 10^6$ of either OT-2 cells or OT-1 TCR transgenic T cells intravenously.

LPS Purification

P. gingivalis strain A7436 (Hirschfeld, M., et al. 2001. "Signaling by toll-like receptor 2 and 4 agonists results in differential gene expression in murine macrophages," *Infect Immun* 69:1477–1482) and E. coli strain 25922 (American Type Culture Collection, Manassas, Va.) were cultured under identical conditions and LPS purified as previously described (Cutler, C. W., et al. 1996. "Hemin-induced modifications of the antigenicity and hemin-binding capacity of *Porphyromonas gingivalis* lipopolysaccharide," *Infect Immun* 64:2282–2287; Westphal, O., and K. Jann. 1965. "Bacterial lipopolysaccharides. Extraction with phenol water and further applications of the procedure," *Methods Carbohydrate Chem* 5:83). LPS extraction was achieved by a hot-phenol-water method, followed by further purification using isopycnic density gradient centrifugation. Briefly, 10 g (wet weight) of bacterial cell pellet was suspended in 35 mL of pyrogen-free water, and then 35 mL of 90% phenol at 65° C. was added dropwise for 20 minutes and stirred constantly. The aqueous phase was separated by centrifugation at 7,000×g for 20 minutes and collected. This process was repeated, and the aqueous phase was pooled and dialyzed against deionized water for 3 days. The dialyzed LPS preparation was then subjected to cesium chloride isopycnic density gradient centrifugation (in 0.5837 g $CsCl_2$ per 4.4 mL of the LPS preparation) at 42,000 rpm for 72 hours in a Beckman L-60 Ultracentrifuge (Palo Alto, Calif.). The refractive indices of the gradient fractions were determined with a refractometer (Milton Roy, Rochester, N.Y.), and values were converted to density (grams per milliliter). Fractions containing LPS (density fractions between 1.42 and 1.52 g/mL) were pooled, dialyzed against distilled water for 3 days, lyophilized and stored at room temperature. LPS was analyzed for protein by the BCA protein assay (Pierce Chemical Company, Rockford, Ill.). LPS samples were also separated by sodium dodecyl-sulfate-polyacrylamide gel electrophoresis (SDS-PAGE) and stained for protein with Coomasie blue (Pierce Chemical Company, Rockford, Ill.). Selected samples were also subjected to proteinase K digestion and nuclease treatment and reanalyzed by SDS-PAGE to confirm the purity of the LPS moieties (Pierce Chemical Company, Rockford, Ill.).

Endotoxin-Free OVA

Chicken OVALBUMIN (OVA) (Sigma Chemical Co., St. Louis, Mo.) was freshly prepared in phosphate buffered saline (PBS) at a concentration of 20 mg/mL, and depleted of the endotoxin activity (measured by LAL QCL-1000 kit from Bio Whittaker, Walkersville, Md., using manufacturer's protocol dated 2000), with the Detoxi-Gel Affinity Pack Columns (Pierce Chemical Company, Rockford, Ill.). After depletion the endotoxin level was below the limit of detection of the LAL QCL-1000 kit (<0.1 EU).

Injections

Reconstituted mice (3–5 per group) were injected either intraperitoneally, or in the footpad, with either 2 mg OVA in saline, 2 mg OVA+25 µg E. coli LPS, or 2 mg OVA+25 µg P. gingivalis LPS. Endotoxin activity in saline was measured by LAL QCL-1000 kit, and observed to be below the detection limit. Prior to mixing with OVA, LPS was sonicated extensively, to ensure uniform mixing of micelles. Footpad injections were given in a volume of 25 µl. Intraperitoneal injections were given in a volume of 100 µl.

Flow Cytometry

For analyses of OT-2 cells from mouse strain 426-6, cell suspensions were prepared from the draining popliteal lymph nodes or spleens, and incubated on ice with PE-labeled anti-Thy1.2 (Pharmingen, San Diego, Calif.), FITC-labeled Vα2 (Pharmingen), Cy-Chrome labeled CD4 (Pharmingen) and Biotin-labeled Vβ5 (Pharmingen), followed by streptavidin allophycocyanin (APC) (Pharmingen). Alternatively, we used antibodies against Thy1.2 and CD4. For analyses of OT-1 cells from OT-1 TCR transgenic mice, cell suspensions of draining popliteal lymph nodes or spleens were stained with PE-labeled anti-Thy1.2 (Pharmingen, San Diego, Calif.), FITC-labeled Vα2 (Pharmingen), and Biotin labeled CD8 (Pharmingen), followed by streptavidin allophycocyanin (Pharmingen). Alternatively, we simply used antibodies against Vα2 and CD8. DCs were stained with FITC-labeled CD11c (Pharmingen), in combination with PE-labeled CD11b (Pharmingen), or biotin-labeled CD8α (Pharmingen), followed by streptavidin allophycocyanin (Pharmingen) using a FACSvantage flow cytometer (Becton Dickinson), equipped with Enterprise II laser (Coherent Radiation, Palo Alto, Calif.).

In Vitro Cultures

Four days after injecting with OVA or OVA+LPS, $2.5 \times 10^5$ popliteal lymph node cells (footpad injections) or splenocytes (intraperitoneal injections) were plated in triplicate in 96-well flat bottomed plates (Costar, Cambridge, Mass.) in 200 µl of RPMI complete medium (GIBCO BRL, Grand Island, N.Y., US) supplemented with 5% fetal bovine serum (FBS), together with different concentrations (0–500 µg/mL of OVA, or OVA peptide (SIINFEKL, SEQ ID NO:1) (New England Peptide Incorporated, Fitchburg, Mass.). Proliferative responses were assessed after 72 hours of culture in a humidified atmosphere of 5% $CO_2$ in air. Cultures were pulsed with 1.0 µCi [$^3$H] thymidine for 12 hours, and incorporation of the radionucleotide was measured by β-scintillation spectroscopy (Pulendran, B., et al. 1999. "Distinct dendritic cell subsets differentially regulate the class of immune response in vivo," Proc Natl Acad Sci USA 96:1036–1041). For cytokine assays, aliquots of culture supernatants were removed after 72 hours, pooled, and assayed for the presence of IFNγ, IL-2, IL-4, IL-5, IL-10, and IL-13 by ELISA.

Cytokine ELISAs

IFNγ, IL-2, IL-10, IL-4, IL-5, IL-6, IL-12, IL-13 and TNFα were quantified by ELISA kits from Pharmingen (San Diego, Calif.) using manufacturer's instructions dated 2000.

Immunohistology/Confocal Microscopy

Cohorts of C57BL/6 mice were injected with either PBS, E. coli LPS (50 µg), or P. gingivalis LPS (50 µg), either intravenously or intraperitoneally. Spleens were removed 6 hours later and embedded in Tissue-Tek OCT compound (Miles, Elkhart, Ind.) by flash freezing in 2-methyl butane (Mallinckrodt, Paris, Ky.) cooled with liquid nitrogen. The frozen tissue was stored at −70° C. Six-micrometer sections were cut on a cryostat (Reichert Jung, Cambridge Instruments GmbH, Germany) and mounted onto poly-L-lysine-coated slides. Sections were air dried for 10 minutes, fixed in ice-cold acetone (Baxter Diagnostics, Deerfield, Ill.) for 10 minutes, air dried and stored.

Splenic sections were rehydrated with PBS, and blocked with PBS/5% bovine serum albumin (BSA)/1% goat serum for 20 minutes, and stained with FITC-conjugated anti-CD11c (Pharmingen, San Diego, Calif.) and PE-conjugated anti-CD4 (Pharmingen, San Diego, Calif.) for 1 hour. The sections were washed and coverslips mounted onto glass slides with Fluoromount (Southern Biotechnology Associates, Birmingham, Ala.). Confocal microscopy was performed using a TCS SP microscope equipped with argon and krypton ion lasers and a 10×HC PL-APO objective (Leica Microsystem, Heidelberg, Germany).

Purification of Dendritic Cells

CD11c+CD8α+ and CD11c+CD8α− DC subsets were purified from spleens as follows. Spleens of C57BL/6 mice were dissected, cut into small fragments and then digested with collegenase D (0.5 mg/mL; Boehringer-Mannheim, Mannheim, Germany) and Dnase I (40 mg/mL, Boehringer-Mannheim) in RPMI 1640 medium supplemented with 5% fetal calf serum (FCS) for 10 minutes at 37° C. Digested fragments were washed twice in PBS/5% FCS. Then, CD11c+ DCs were enriched using CD11c+ microbeads (Miltenyi Biotech, San Diego, Calif.). The enriched DCs were stained with FITC-conjugated CD11c (Pharmingen) and PE-conjugated CD8α+ (Pharmingen) and sorted into the CD11c+ CD8α+ and CD11c+ CD8α− subsets, using a FACSvantage flow cytometer (Becton Dickinson), equipped with Enterprise II laser (Coherent Radiation, Palo Alto, Calif.).

Induction of Cytokines from DC Subsets

CD11c+ CD8α+ and CD11c+ CD8α− DCs were isolated by flow cytometry and cultured in RPMI complete medium supplemented with 5% FBS and with either 10 µg/mL E. coli LPS or 10 µg/mL P. gingivalis LPS for 24 hours or 48 hours.

EXAMPLE 1

E. coli LPS and P. gingivalis LPS Enhance Antigen-Specific T-Helper Responses In Vivo We demonstrated that LPS from E. coli and P. gingivalis could enhance antigen-specific T-helper responses against a soluble protein using OVA as an example. We utilized OVA-specific, MHC class II-restricted (1-$A^b$), αβ T cell receptor (TCR) transgenic mice (OT-2 mice) because the CD4+OVA-specific T cells express Vα2 and Vβ5 (Barnden, M. J., et al. 1998. "Defective TCR expression in transgenic mice constructed using cDNA-based alpha- and beta-chain genes under the control of heterologous regulatory elements," Immunol Cell Biol 76:34–40). TCR transgenic T cells were adoptively transferred into Thy-1 congenic B6.PL.THY1$^a$ (B6.PL) mice, such that they constituted a small but detectable proportion of all T cells (Kearney, E. R., et al. 1995, "Antigen-dependent clonal expansion of a trace population of antigen-specific CD4+ T cells in vivo is dependent on CD28 costimulation and inhibited by CTLA-4," J Immunol 155:1032–1036). In this system, the fate of OVA-specific, transgenic T cells was followed using the Thy1.2 antibody, which stains only the transferred cells. T cells with the phenotype Thy1.2+ CD4+ Vα2+ Vβ5+ was considered OVA-specific CD4+ T cells.

Figure 2:
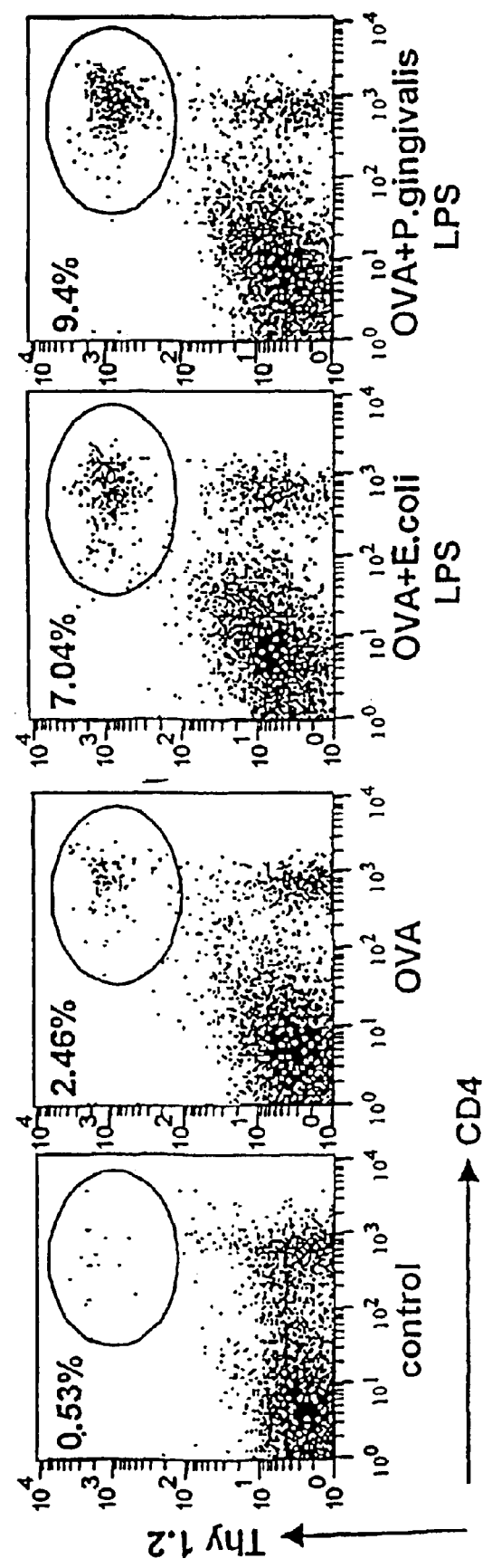
FIGS. 2A–2G depict *E. coli* LPS and *P. gingivalis* LPS enhancing antigen-specific T-helper responses in vivo. B6.PL.THY1$^a$ (B6.PL) mice reconstituted with OT-2 transgenic T cells were immunized with soluble OVA, *E. coli* LPS alone, *P. gingivalis* LPS alone, OVA+*E. coli* LPS, or OVA+*P. gingivalis* LPS, either subcutaneously in the footpad (FIGS. 2B, 2D and 2F) or intraperitoneally (FIGS. 2C, 2E and 2G). Four days later, the draining popliteal lymph nodes (subcutaneous route), or spleens (intraperitoneal route) were removed, and the clonal expansion of OVA-specific CD4+ T cells assessed by flow cytometry, by staining with Thy1.2 versus CD4.
Figure 2:
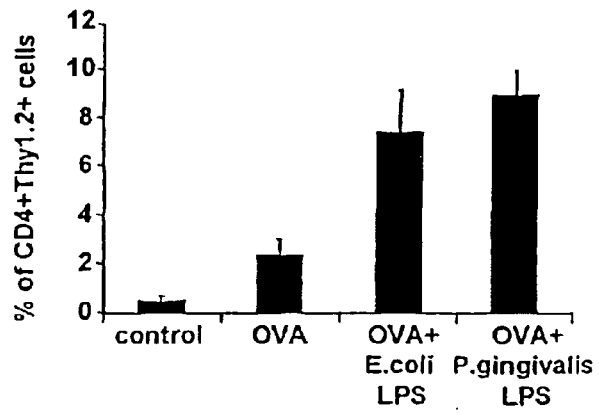
Figure 2:
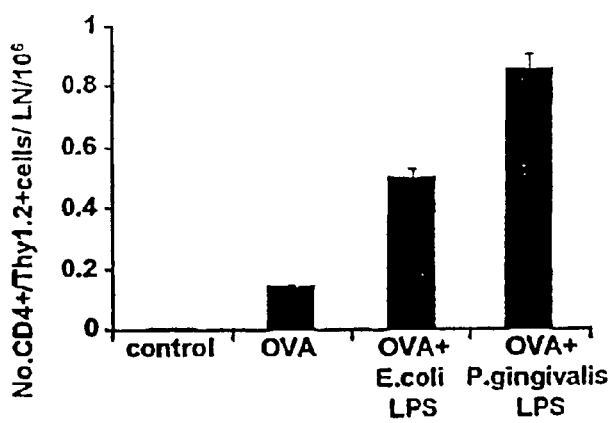
Figure 2:
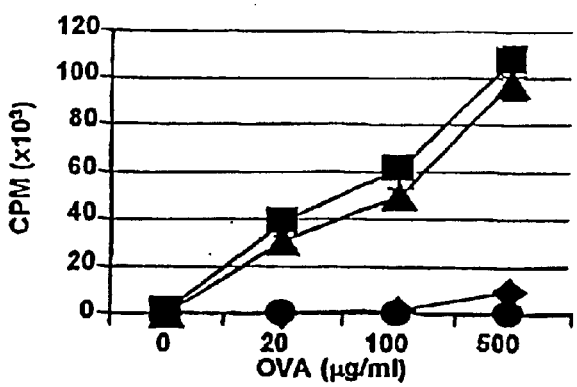
Figure 2:
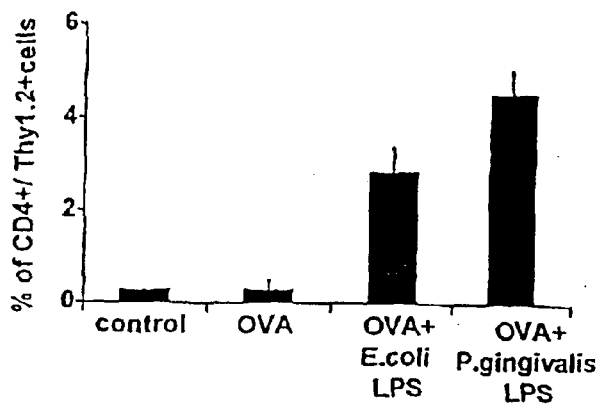
Figure 2:
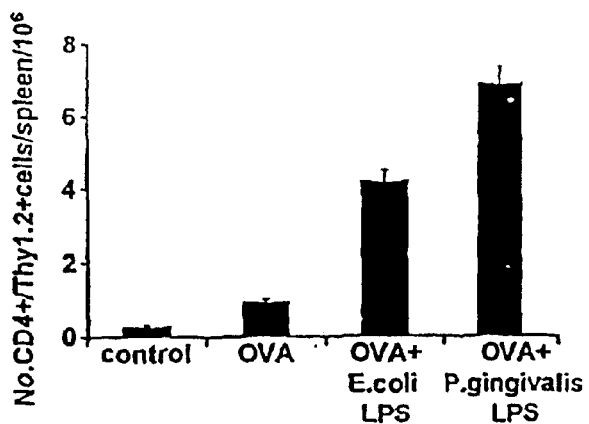
Figure 2:
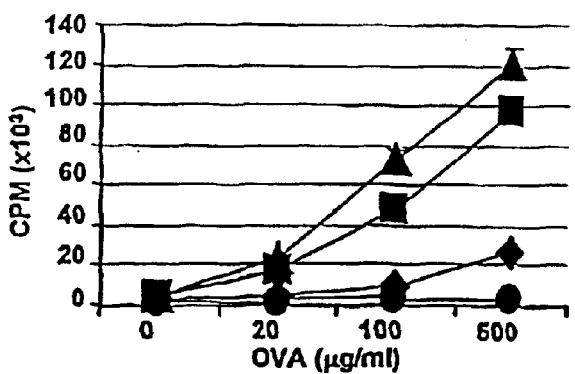
Figure 3:
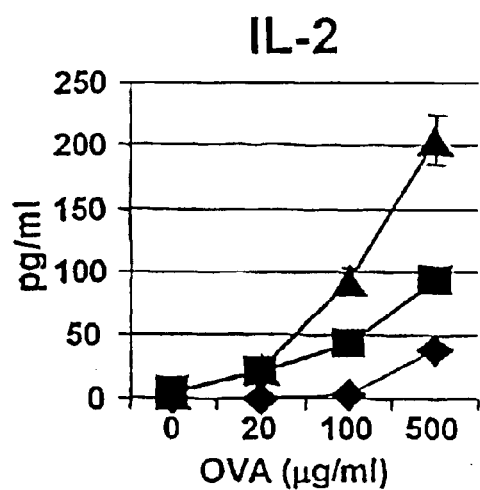
FIGS. 3A–3H depict *E. coli* LPS and *P. gingivalis* LPS inducing distinct types of antigen-specific T-helper responses in vivo. Culture supernatants from the cultures described in FIG. 2F (subcutaneous injection) and FIG. 2G (intraperitoneal injection) were assayed for IL-2 (FIGS. 3A and 3E), IFNγ (FIGS. 3B and 3F), IL-10 (FIGS. 3C and 3G), IL-4 (data not shown), and IL-5 (FIGS. 3D and 3H) with ELISA. Injections of *E. coli* LPS alone or *P. gingivalis* LPS alone did not result in significant cytokine production. The data presented in FIGS. 3A–3H are representative of ten independent experiments.
Figure 3:
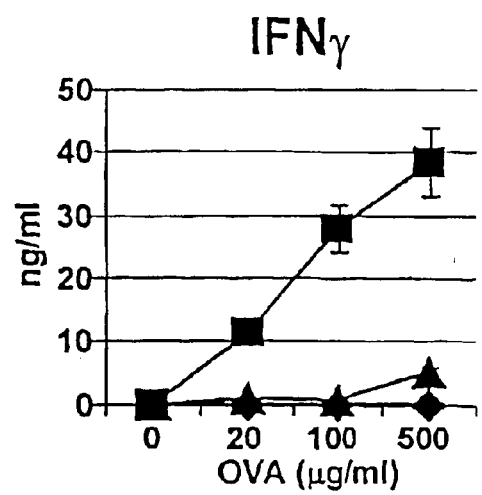
Figure 3:
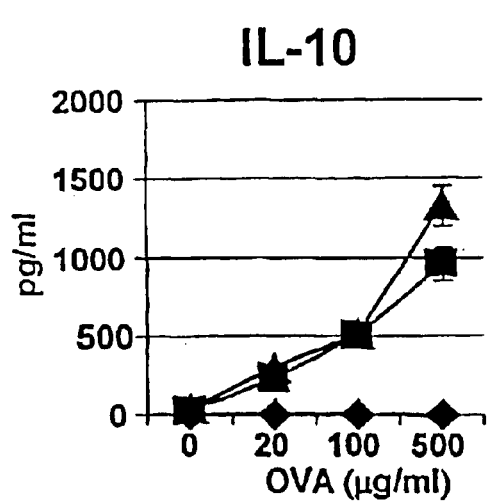
Figure 3:
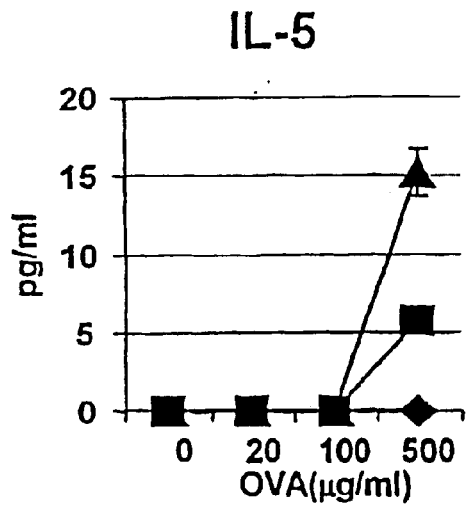
Figure 3:
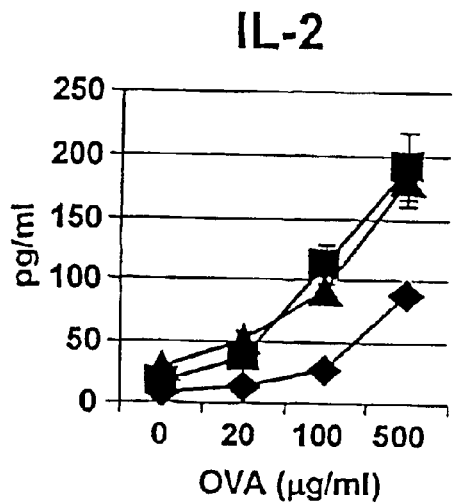
Figure 3:
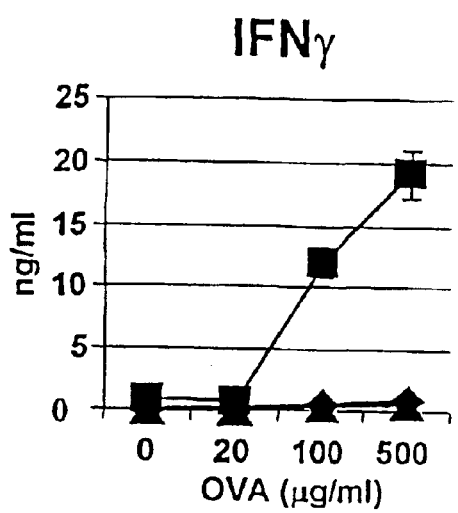
Figure 3:
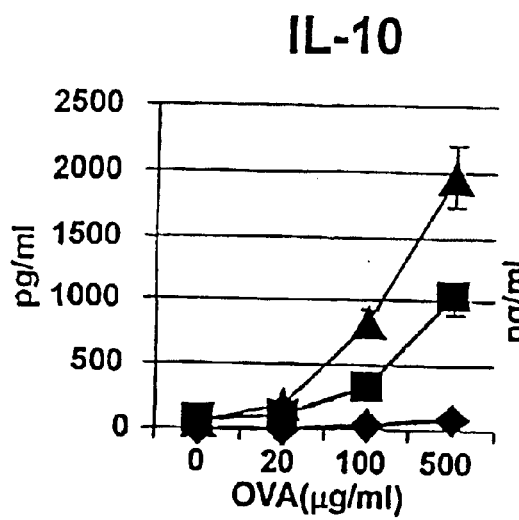
Figure 3:
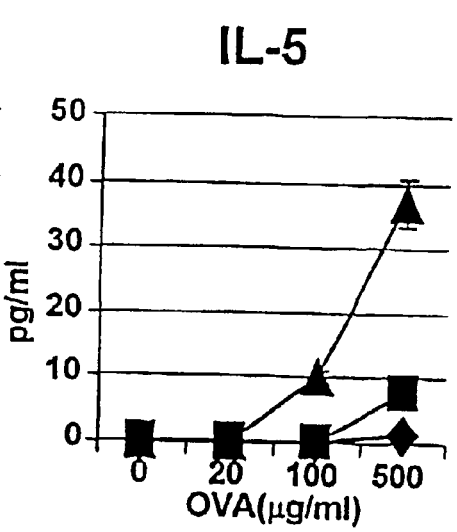

The reconstituted mice were injected with one of the following compositions: soluble endotoxin-free OVA, E.

coli LPS alone, P. gingivalis LPS alone, OVA+E. coli LPS, or OVA+P. gingivalis LPS. Injections were either intraperitoneal or in a footpad (FIG. 1). Prior to the injection, the OVA was depleted of endotoxin contamination using methods described above. The CD4+ OVA-specific T cell response in either the draining lymph nodes or in the spleen was monitored by flow cytometry (FIG. 2A). Injection of OVA elicited a significant clonal expansion of the Thy 1.2+ CD4+ T cells in the draining lymph nodes from mice injected in a footpad FIGS. 2A, 2B and 2D or intraperitoneally FIGS. 2C and 2E. However, P. gingivalis LPS was marginally more effective than E. coli LPS in enhancing the clonal expansion when the antigen was delivered subcutaneously (7.0% OVA+E. coli LPS versus 9.4% OVA+P. gingivalis LPS; FIGS. 2B and 2D).

We next demonstrated the in vitro proliferative capacity of the OVA-specific T cells from the cohorts of mice as well as the effect of the adjuvant in eliciting an immune response. Single cell suspensions of the draining lymph nodes were cultured with varying concentrations of OVA as described above. As shown in FIGS. 2F and 2G, mice that received an injection of OVA+E. coli LPS or OVA+P. gingivalis LPS had a greatly enhanced proliferative response compared with the mice that received OVA alone.

EXAMPLE 2

E. coli LPS and P. gingivalis LPS Induce Distinct Types of Antigen-Specific T-Helper Responses In Vivo Cytokine production by antigen-specific T cells was measured by assaying the culture supernatants from the single cell suspensions of the draining lymph nodes described above for IL-2, IFNγ, IL-4, IL-10 and IL-5. Assessment of cytokine production in these cultures revealed significant differences between mice injected with OVA, OVA+E. coli LPS, or OVA+P. gingivalis LPS (FIGS. 3A–3H). In cultures from mice injected with OVA alone, there was little, if any, IL-2, IFNγ, IL-10, IL-4, or IL-5 produced. In contrast, in cultures from mice injected with OVA+E. coli LPS, there was significant IL-2 and IL-10 and very high levels of IFNγ produced by the antigen-specific T cells. Neither IL-4 nor IL-5 could be detected in cells from OVA+E. coli LPS injected mice.

In cultures from mice injected with OVA+P. gingivalis LPS, there was a striking diminution of IFNγ production, despite significant production of IL-2 and Th2 cytokines IL-10 and IL-5 (FIGS. 3A–3H). In fact, the level of IFNγ was as low as that observed with OVA alone. Therefore, while both types of LPS elicit potent clonal expansion of antigen-specific CD4+ T cells in vivo, E. coli LPS induces a Th1-like response, characterized by high levels of IFNγ. In contrast, P. gingivalis LPS induces a response that is essentially devoid of IFNγ and characterized by significant levels of IL-10 and IL-5. It should be noted that the route of injection did not affect the pattern of cytokine production (FIGS. 3A–3H). No significant levels of IL-4 could be detected in any of the conditions, which may reflect the Th1 bias of the C57BL/6 strain utilized.

EXAMPLE 3

E. coli LPS and P. gingivalis LPS Enhance Antigen-Specific CD8+ T-Cell Responses In Vivo The dramatically different immune responses induced by E. coli LPS and P. gingivalis LPS suggested that there may be differences in antigen-specific CD8+ T cell responses. Using OT-1 mice (H12K$^b$ restricted, OVA-specific TCR-transgenic mice), we demonstrated that the distinct immune responses elicited by the different LPS molecules are due to the differences in antigen-specific CD8+ T cell responses (Hogquist, K. A., et al. 1994. "T cell receptor antagonist peptides induce positive selection," Cell 76:17–27; Martin, S. and M. J. Bevan 1997. "Antigen-specific and nonspecific deletion of immature cortical thymocytes caused by antigen injection," Eur J Immunol 27:2726–2736). Spleen cells (5×10$^6$) from OT-1 mice (B6.PL, Thy1.2) were adoptively transferred into B6.PL (Thy 1.1) hosts. Cohorts of host mice were injected with one of the following compositions: OVA, OVA+E. coli LPS, or OVA+P. gingivalis LPS. Clonal expansion of OVA-specific CD8+ T cells Thy1.2+, Vα2+ CD8+ was assessed by flow cytometry (FIGS. 4A–4E). Both E. coli LPS and P. gingivalis LPS adjuvants enhanced the clonal expansion of OVA-specific CD8+ T cells.

Figure 4:
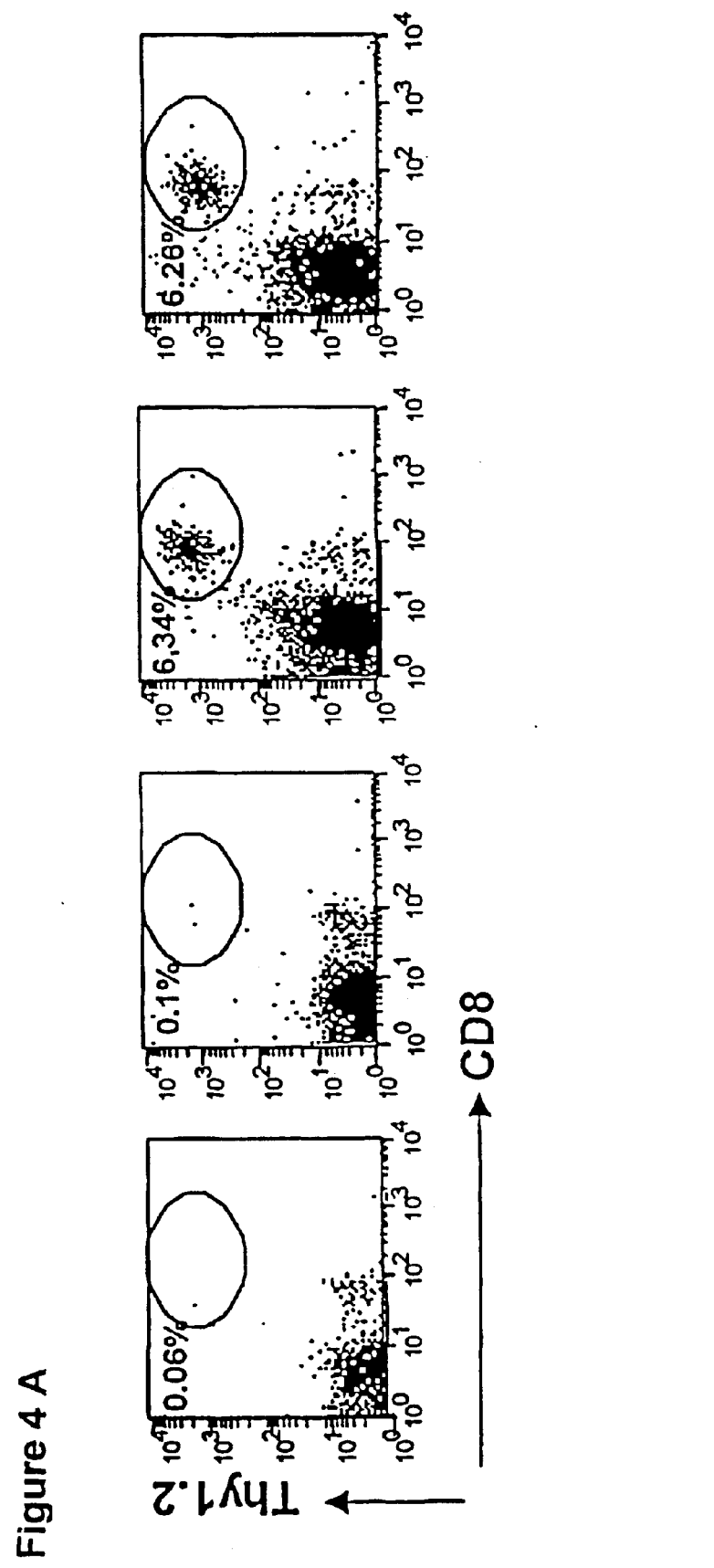
FIGS. 4A–4G depict E. coli LPS and P. gingivalis LPS enhancing antigen-specific CD8+ T-cell responses in vivo. C57BL/6 mice, or B6.PL.THY1$^a$ (B6.PL) mice reconstituted with OT-1 transgenic T cells were immunized with soluble OVA, OVA+E. coli LPS, or OVA+P. gingivalis LPS, either subcutaneously in the footpad (FIGS. 4B, 4D and 4F) or intraperitoneally (FIGS. 4C, 4E and 4G). Four days later, the draining popliteal lymph nodes (footpad injections) or spleens (intraperitoneal route) were removed, and the clonal expansion of OVA-specific CD8+ T cells assessed by flow cytometry, by staining with CD8 versus Vα2, or CD8 versus Thy1.2 versus Vα2.
Figure 4:
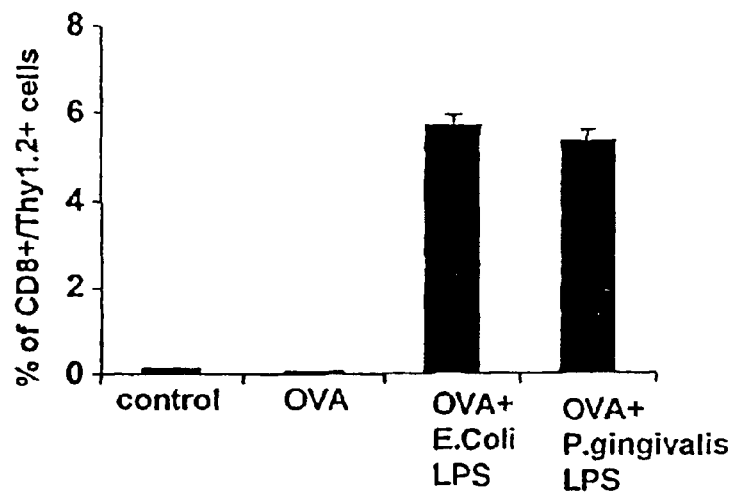
Figure 4:
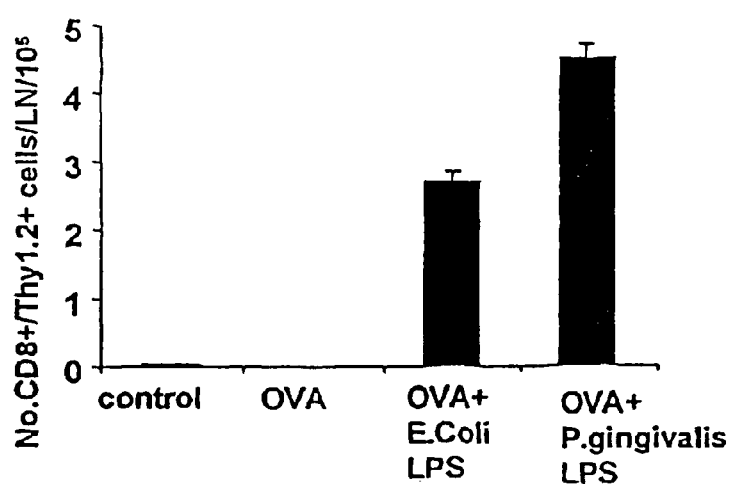
Figure 4:
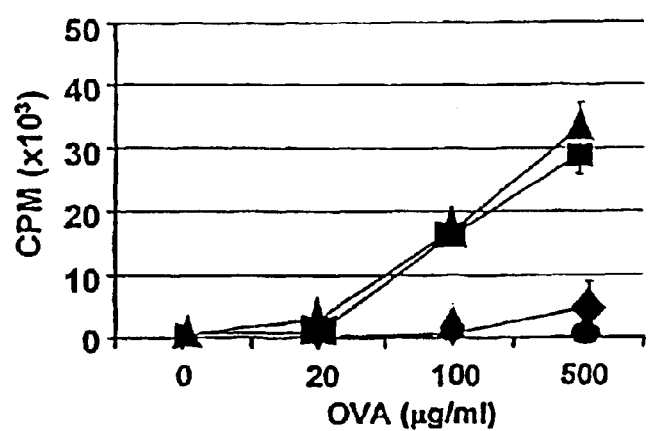
Figure 4:
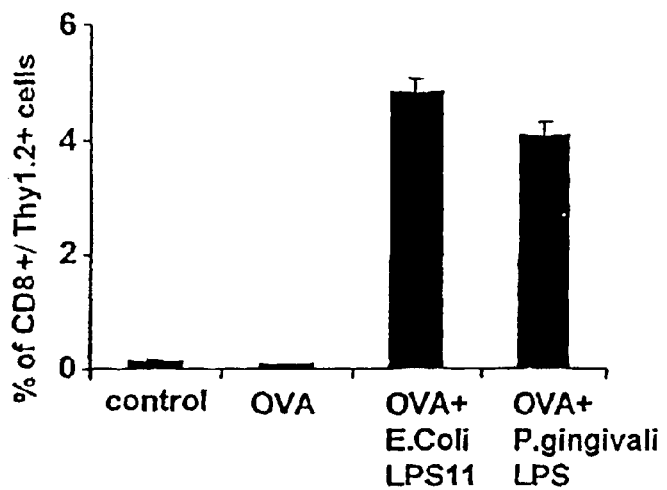
Figure 4:
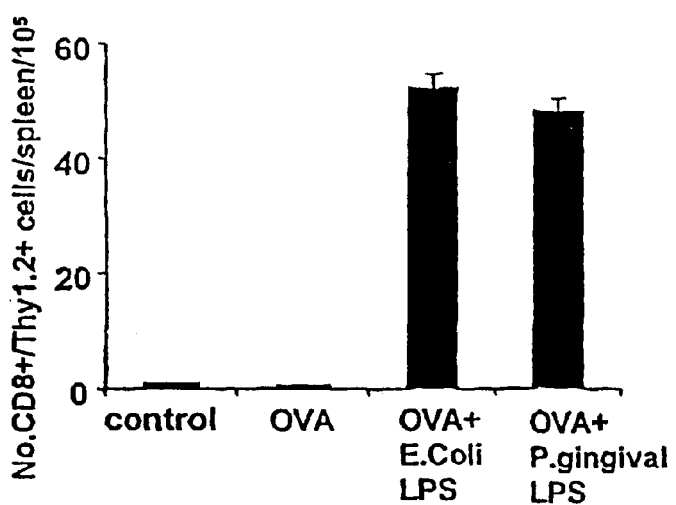
Figure 4:
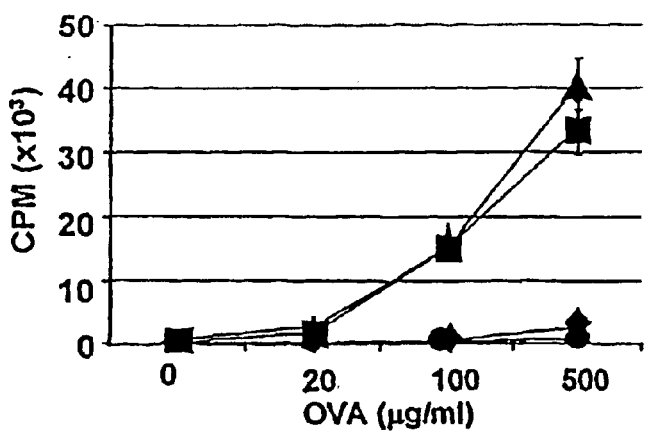

Next, we demonstrated the in vitro proliferative capacity of the OVA-specific CD8+ T cells from the cohorts of mice by culturing single cell suspensions of the draining lymph nodes (subcutaneous route), or spleen (intraperitoneal route) with varying concentrations of OVA. As shown in FIGS. 4F and 4G, mice that received an injection of either OVA+E. coli LPS or OVA+P. gingivalis LPS had greatly enhanced proliferative responses, compared to cells from mice who received OVA alone.

EXAMPLE 4

Figure 5:
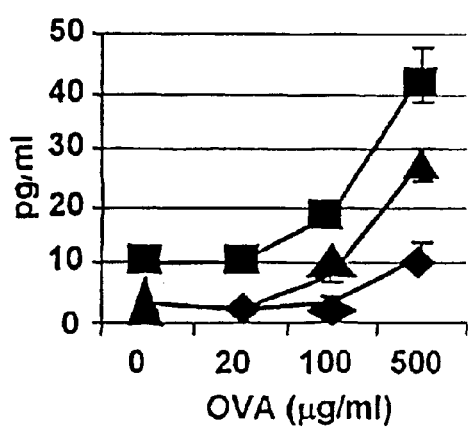
FIGS. 5A–5H depict E. coli LPS and P. gingivalis LPS inducing distinct types of antigen-specific CD8+ T-cell responses in vivo. Culture supernatants from the cultures described in FIGS. 3E and 3F were assayed for IL-2 (FIGS. 5A and 5E), IFNγ (FIGS. 5B and 5F), IL-10 (FIGS. 5C and 5G), IL-4 (data not shown), and IL-5 (FIGS. 5D and 5H) with ELISA. Injections of E. coli LPS alone or P. gingivalis LPS alone did not result in significant cytokine production (data not shown). The data presented in FIGS. 5A–5H are representative of three independent experiments.
Figure 5:
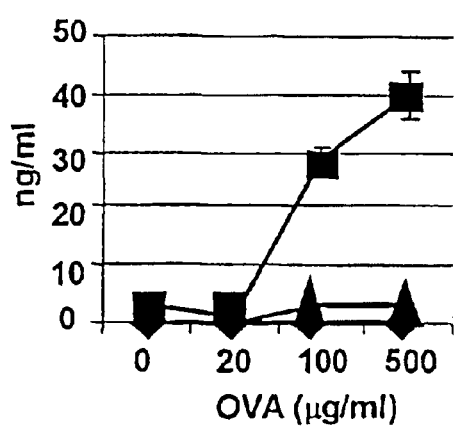
Figure 5:
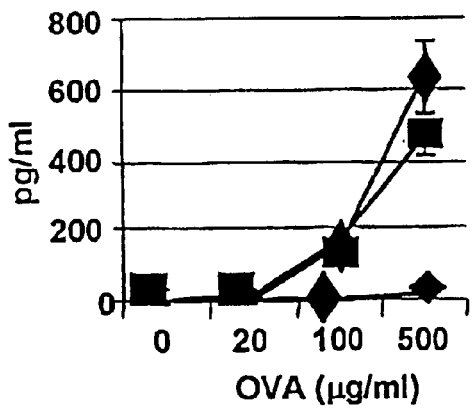
Figure 5:
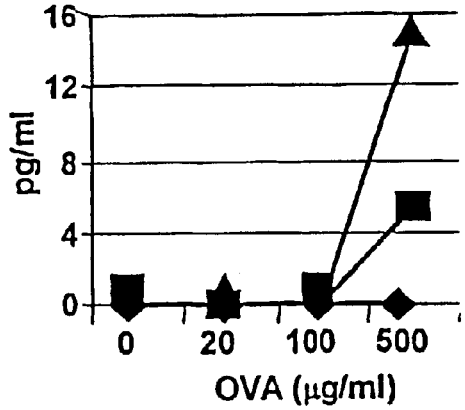
Figure 5:
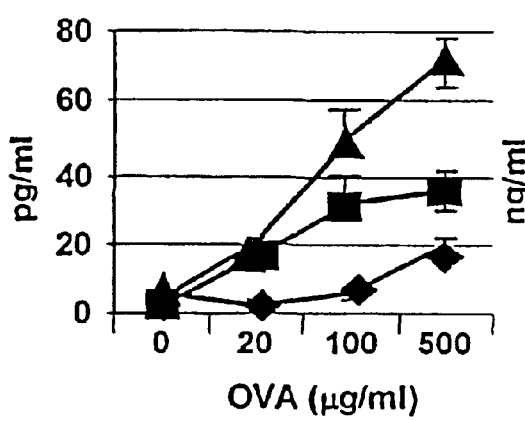
Figure 5:
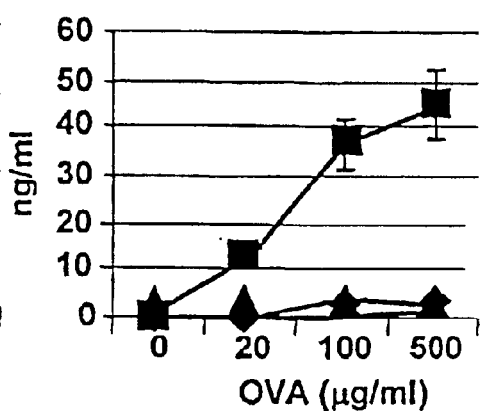
Figure 5:
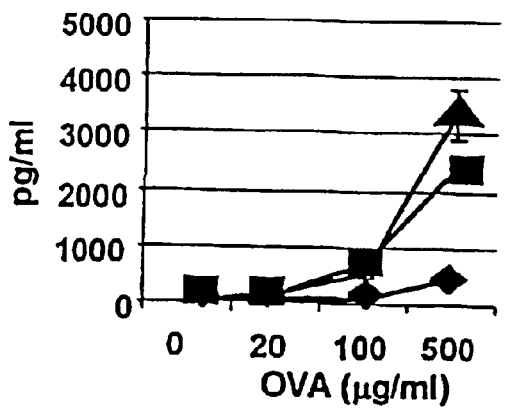
Figure 5:
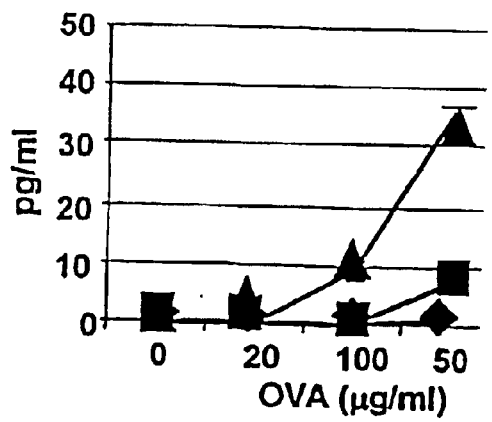

E. coli LPS and P. gingivalis LPS Induce Distinct Types of Antigen-Specific CD8+ T-Cell Responses In Vivo We next examined the cytokines produced in CD8+ T-cell cultures by ELISA. As observed with the CD4+ OT-2 cells, CD8+ OT-1 cells stimulated with OVA alone did not secrete significant levels of IL-2, IFNγ, IL-10, or IL-5 (FIGS. 5A–5H). Cells from mice injected with OVA+E. coli LPS produced very high levels of IFNγ (FIGS. 5B and 5F) and significant levels of IL-10 (FIGS. 5C and 5G), but no IL-5 (FIGS. 5D and 5H). In contrast, cells from mice injected with OVA+P. gingivalis LPS produced much lower levels of IFNγ (FIGS. 5B and 5F), but significant levels of IL-10 (FIGS. 5C and 5G) and IL-5 (FIGS. 5D and 5H), consistent with the cytokine patterns observed with CD4+ OT-2 cells (FIGS. 3A–3H). No significant levels of IL-4 were detected in any condition.

EXAMPLE 5

Both E. coli LPS and P. gingivalis LPS Activate CD8α+ and CD8α− DC Subsets In Vivo All known adjuvants in the prior art are known to non-specifically activate DCs, thereby enhancing T-cell immunity (Reis e Sousa, C. and R. N. Germain. 1999. "Analysis of adjuvant function by direct visualization of antigen presentation in vivo: endotoxin promotes accumulation of antigen-bearing dendritic cells in the T cell areas of lymphoid tissue," J Immunol 162:6552–6561). We demonstrated that LPS originating from both E. coli and P. gingivalis were capable of activating DC subsets in vivo. C57BL/6 mice were injected with 25 µg of E. coli LPS or P. gingivalis LPS, either subcutaneously, intraperitoneally, or intravenously, and sacrificed 6 hours later. Spleens and lymph nodes were collected, and the expression of activation or maturation markers (CD80, CD86 and CD40) on DCs were determined.

CD8α+ and myeloid CD8α– DCs from the spleens of PBS treated control mice express significant levels of CD80, CD86 and CD40 as reported previously (Pulendran, B., J., et al. 1997 "Developmental pathways of dendritic cells in vivo: distinct function, phenotype, and localization of dendritic cell subsets in FLT3 ligand-treated mice" *J Immunol* 159:2222–2231). In addition to this observation, upon injection of either type of LPS, there was a significant up-regulation of CD80, CD86 and CD40 on both DC subsets (FIGS. 6A–6L). Therefore, both types of LPS appear to activate the CD8α+ and CD8α– DC subsets in vivo.

EXAMPLE 6

*E. coli* LPS, But Not *P. gingivalis* LPS Induces IL-12 in CD8α+ DCs

Figure 7:
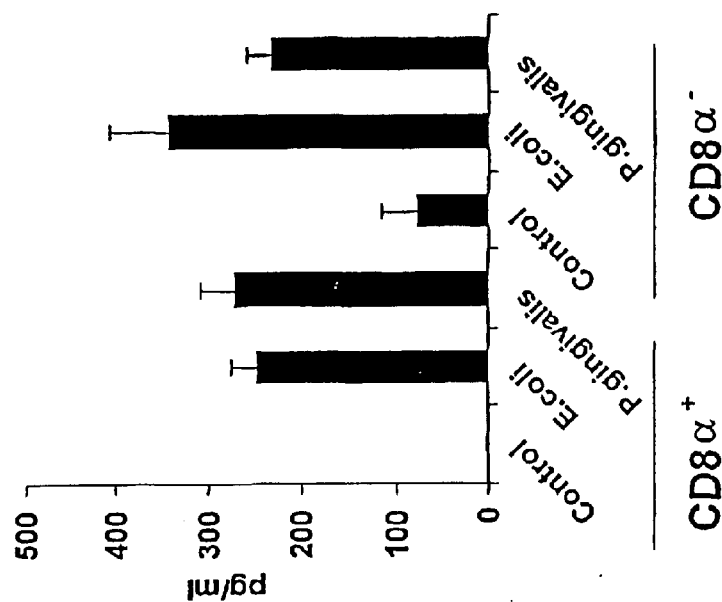
FIGS. 7A–7C depict E. coli LPS, but not P. gingivalis LPS inducing IL-12 in CD8α+ DCs. Splenic CD11c+ CD8α+ and CD11c+CD8α DCs were isolated from C57BL/6 mice by microbead enrichment, followed by flow cytometry and stimulated in vitro with 10 μg/mL of E. coli LPS or P. gingivalis LPS. Culture supernatants were assayed for IL-12 (FIG. 7A), IL-6 (FIG. 7B), or TNFα (FIG. 7C) 24 hours later. The data presented in FIGS. 7A–7C are representative of ten independent experiments.
Figure 7:
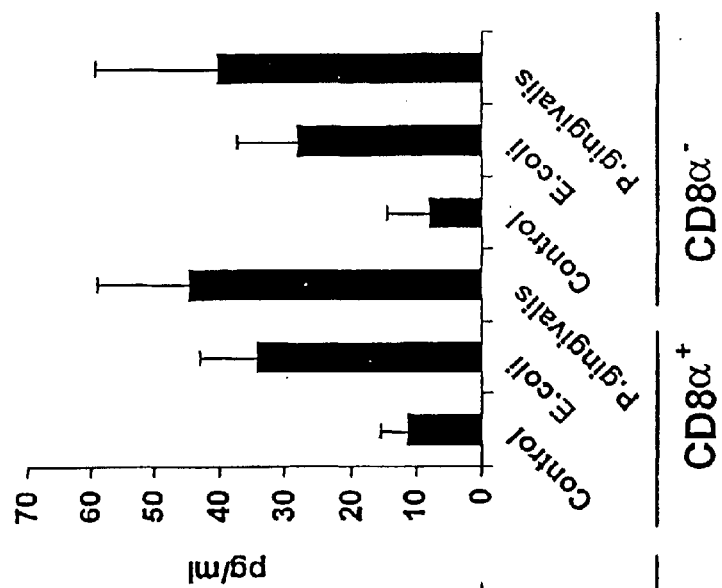
Figure 7:
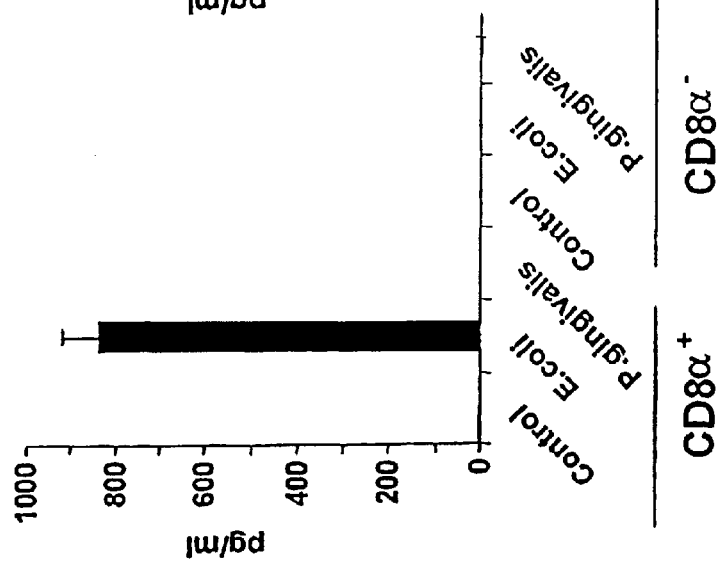

We demonstrated that IL-12 production in CD8α+ DCs only occurred with LPS from *E. coli*. DCs were enriched from the spleens of C57BL/6 mice as described previously. The CD11c+ CD8α+ and CD11c+ CD8α– DC subsets were isolated by flow cytometry, and cultured for 24 hours without additional material or with either *E. coli* LPS or *P. gingivalis* LPS. The supernatants were then assayed for the presence of IL-12, IL-6, and TNFα by ELISA. Both types of LPS induced IL-6, and TNFα in both DC subsets, but only *E. coli* LPS induced IL-12 in the CD8α+ DC subset (FIG. 7A). Therefore, while both types of LPS could activate both DC subsets, only the *E. coli* LPS could elicit the Th1 inducing cytokine IL-12. Although IL-10 and IL-13 may be Th2-inducing cytokines, significant levels of either IL-10 or IL-13 could not be consistently detected in these cultures.

EXAMPLE 7

Figure 8:
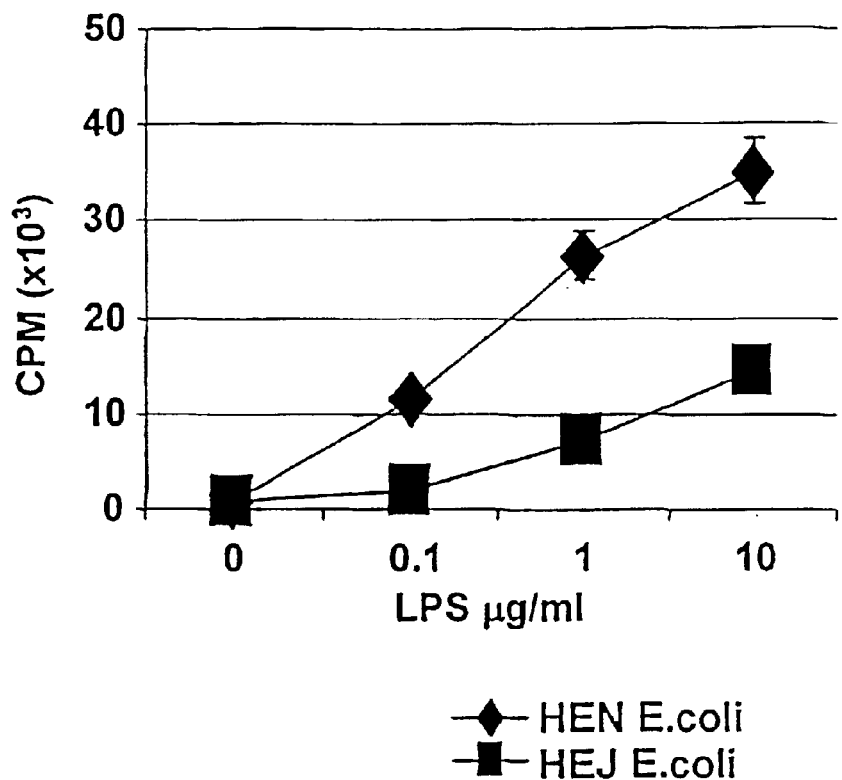
FIGS. 8A and 8B demonstrate that TLR4 is the dominant receptor for signaling mediated by E. coli LPS, but not for P. gingivalis LPS. Splenocytes from C3H/HeJ mice and C3H/HeN mice were cultured with varying concentrations of E. coli LPS (FIG. 8A) or P. gingivalis LPS (FIG. 8B) for 72 hours. The cultures were pulsed with [$^3$H] during the last 12 hours of culture. The data presented in FIGS. 8A–8B are representative of three independent experiments.
Figure 8:
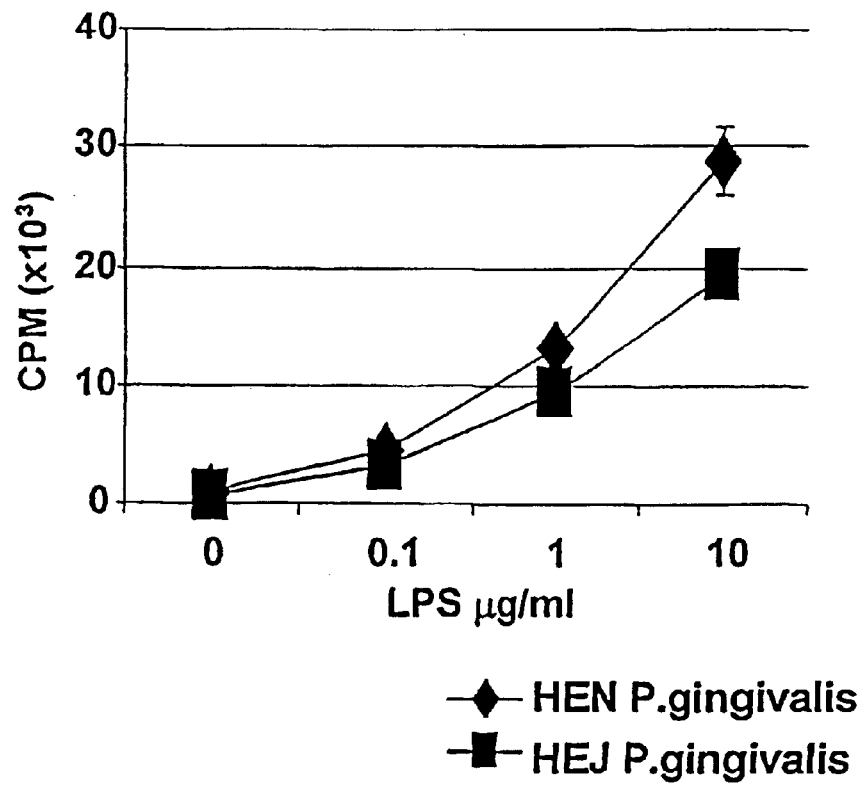
Figure 9:
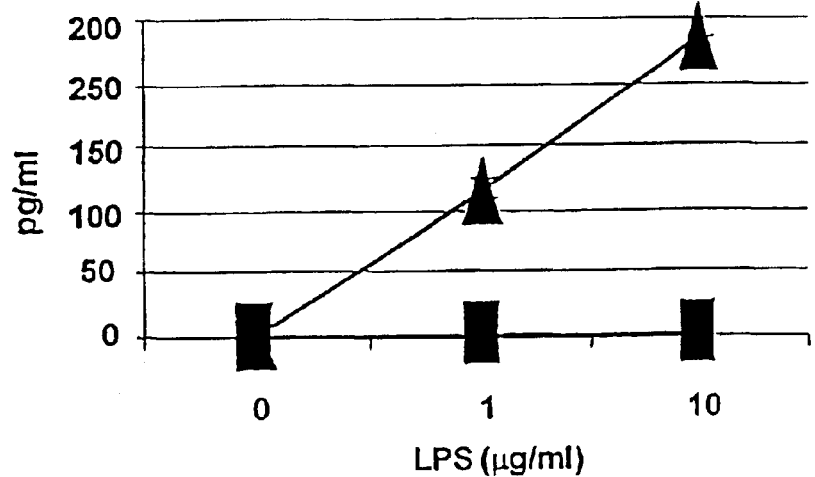
FIGS. 9A–9D depict IL-6 production by splenocytes stimulated with E. coli LPS or P. gingivalis LPS in C3H/HeN and C3H/HeJ mice. Splenocytes from C3H/HeJ mice and C3H/HeN mice were cultured with varying concentrations of E. coli LPS for 12 hours or 48 hours (FIG. 9A and FIG. 9C, respectively) or P. gingivalis LPS for 12 hours or 48 hours (FIGS. 9B and 9D, respectively). IL-6 was measured by cytokine ELISA. The data presented in FIGS. 9A–9B are representative of three independent experiments.
Figure 9:
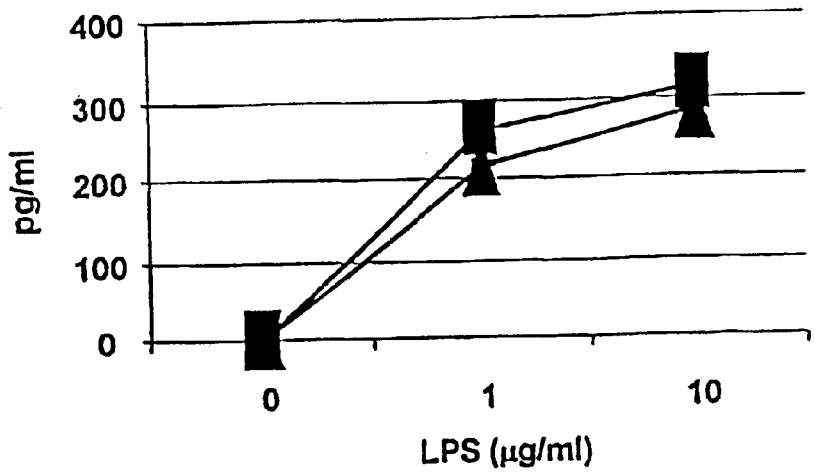
Figure 9:
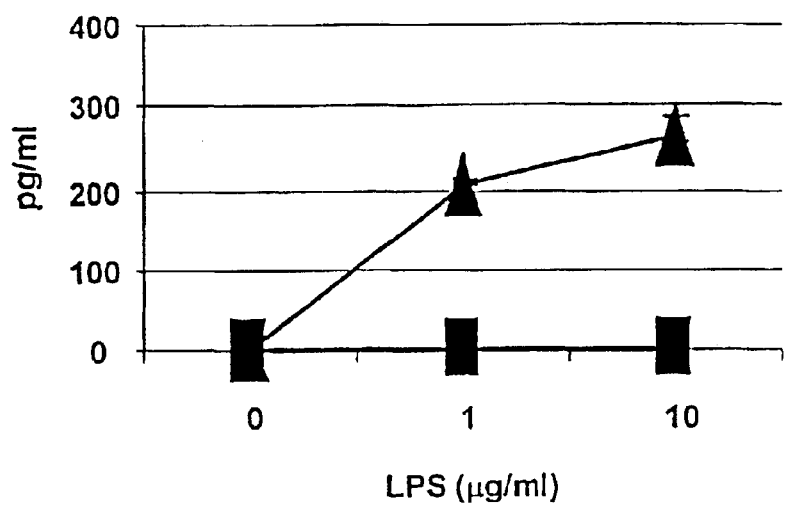
Figure 9:
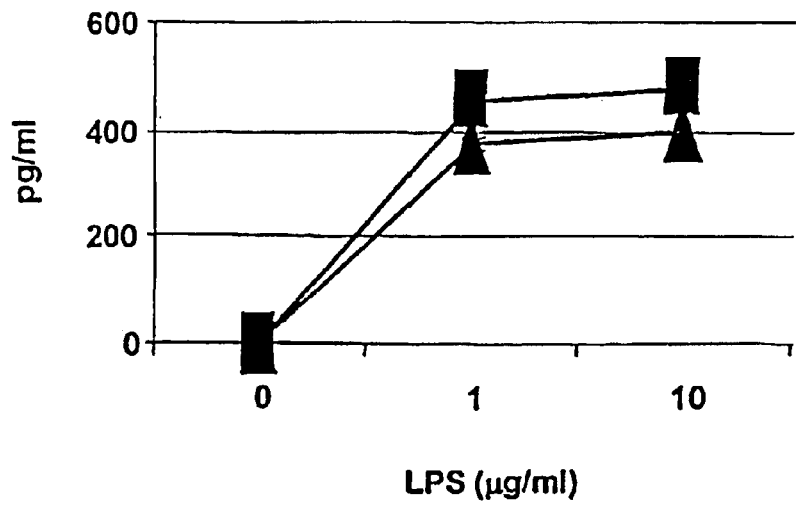

TLR4 is the Dominant Receptor for Signaling Mediated by *E. coli* LPS, But Not for *P. gingivalis* LPS Although *E. coli* LPS mediates its effects by signaling through Toll-like receptor 4 (TLR4), *P. gingivalis* LPS may signal through a TLR4-independent mechanism. We determined the effect of either type of LPS on proliferation of splenocytes from TLR4 deficient mice (C3H/HeJ mice) and wild type (C3H/HeN) mice. C3H/HeJ splenocytes cultured with *E. coli* LPS were greatly impaired in their proliferative capacity, compared to the C3H/HeN controls (FIG. 8A). In contrast, C3H/HeJ splenocytes cultured with *P. gingivalis* LPS were only modestly impaired in their proliferative capacity, compared to the C3H/HeN controls (FIG. 8B). Consistent with this, production of IL-6 induced by *E. coli* LPS was greatly impaired in C3H/HeJ splenocytes, compared to C3H/HeN splenocytes (FIGS. 9A and 9C). However, production of IL-6 induced by *P. gingivalis* LPS was not impaired in C3H/HeJ mice (FIGS. 9B and 9D). Therefore, as reported previously, while *E. coli* LPS signaling is largely dependent on TLR4, *P. gingivalis* LPS appears to signal mainly through a TLR4-independent mechanism. Therefore, as reported previously, *E. coli* LPS signaling is largely dependent on TLR4, whereas *P. gingivalis* LPS appears to signal mainly through a TLR4-independent mechanism.

EXAMPLE 8

*P. gingivalis* LPS, But Not *E. coli* LPS, Stimulates IL-13 Production

Figure 10:
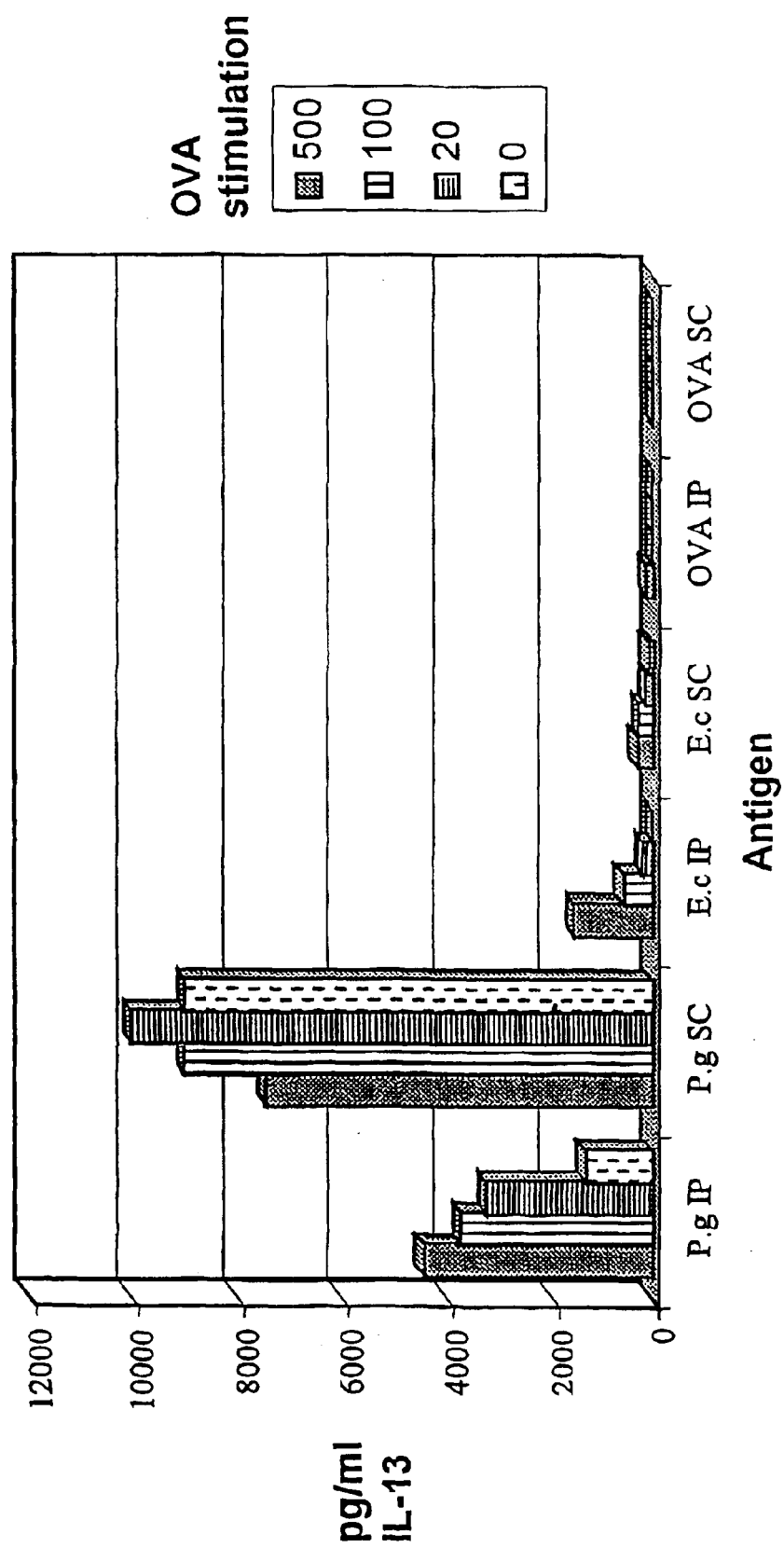
FIG. 10 depicts P. gingivalis LPS inducing much greater levels of IL-13 than E. coli LPS. B6.PL.THY1$^a$ (B6.PL) mice reconstituted with OT-2 transgenic T cells were immunized with soluble OVA, E. coli LPS alone, P. gingivalis LPS alone, OVA+E. coli LPS, or OVA+P. gingivalis LPS, either subcutaneously in the footpad or intraperitoneally. Four days later, the draining popliteal lymph nodes (subcutaneous route), or spleens (intraperitoneal route) were removed, and single cell suspensions were restimulated with varying concentrations of OVA (0–500 μg/mL) for 72 hours, and pulsed with [$^3$H] for 12 hours. The cell populations were then assayed for IL-13 with ELISA. The data presented in FIG. 10 are representative of two independent experiments.

We next demonstrated that IL-13 production is stimulated by the adjuvant *P. gingivalis* LPS. Cytokine production by antigen-specific T cells was measured by assaying the culture supernatants from the single cell suspensions of the draining lymph nodes cultured with varying concentrations of OVA (0–500 μg/mL). Assessment of cytokine production in these cultures revealed significant differences between B6.PL.THY1$^a$ (B6.PL) mice injected with OVA, OVA+*E. coli* LPS, or OVA+*P. gingivalis* LPS and the route of administration (FIG. 10). In cultures from mice injected with OVA alone intraperitoneally or subcutaneously, there was little, if any, IL-13, produced. In contrast, in cultures from mice injected intraperitoneally with OVA+*E. coli* LPS, there was significant IL-13 produced by the antigen-specific T cells. Cultures from mice injected subcutaneously with OVA+*E. coli* LPS did not greatly increase IL-13 production.

In cultures from mice injected with OVA+*P. gingivalis* LPS, there was striking increase of IL-13 production (FIG. 10). Mice injected subcutaneously with OVA+*P. gingivalis* LPS produced much greater IL-13 than those mice injected intraperitoneally. However, even the intraperitoneal injection of OVA+*P. gingivalis* LPS produced much greater IL-13 than those mice injected with OVA+*E. coli* LPS. The production of IL-13, a specific cytokine for the Th2 immune response, in response to *P. gingivalis* LPS injection and not *E. coli* LPS injection, further demonstrates the selective Th2 immune response elicitation of *P. gingivalis* LPS.

Examples 1–8 have demonstrated that different microbial products may induce distinct types of immune responses via differential activation of DC subsets. *E. coli* LPS induced Th1 and Tc1 responses, with high levels of IFNγ, but no IL-4 or IL-5. In contrast, *P. gingivalis* LPS induced Th2 and Tc2 immune responses characterized by significant levels of IL-10, IL-13, and IL-5, but very little or no IFNγ. We have shown, for the first time, an adjuvant which selectively induces the Th2 immune response. The subject of Examples 9–12 is the application of the ability to selectively activate the Th2 immune response rather than the Th1 immune response. The subject matter of Examples 9–12 is meant to be illustrative and in no way limit the application of using *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof, to induce a Th2 immune response. It should also be understood to those skilled in the art that the applications described herein are not limited to humans.

EXAMPLE 9

Use of Adjuvant to Elicit Th2 Immune Response

The invention contemplates a method to elicit a Th2 or Th2-like immune response in a subject who suffers from a disease state that can be alleviated at least in part with an appropriate Th2 or Th2-like immune response. After identifying a disease state that may be alleviated at least in part with a Th2 or Th2-like immune response, the next step may be to determine disease specific antigens. The subsequent step may be to co-administer the disease specific antigens with *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, mimetics thereof, or any combination thereof, to induce a Th2 immune response. Co-administration of disease specific antigens and adjuvants of the present invention that elicit a Th2 or Th2-like immune response can be sequentially or concurrently delivered

EXAMPLE 10

Modulating the Balance of Th1 and Th2 Immune Responses for Treating Disease States The invention contemplates a method to elicit a Th2 or Th2-like immune response in a subject who suffers from a disease state in which an inappropriate Th1 immune response is associated. The method can be implemented to alleviate at least in part an inappropriate Th1 immune response by shifting the response away from the Th1 to a Th2 or Th2-like immune response. After identifying a disease state that may be alleviated at least in part with a Th2 or Th2-like immune response, the next step may be to determine disease specific antigens. The subsequent step may be to co-administer the disease specific antigens with P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof, to induce a Th2 immune response. Co-administration of disease specific antigens and adjuvants of the present invention that elicit a Th2 or Th2-like immune response can be sequentially or concurrently delivered intravenously, intra-arterially, intra-muscularly, intra-dermally, intra-tumorally, or orally. Any pharmaceutical carrier or diluent that maintains the solubility of the components can be used.

EXAMPLE 11

Using P. gingivalis LPS in Conjunction with Other Adjuvants to Elicit a Combined Th1/Th2 Immune Response The invention contemplates a method to elicit both a Th1 and a Th2 or Th2-like immune response in a subject who suffers from a disease state that can be alleviated at least in part with a combined Th1 and Th2 or Th2-like immune response. After identifying a disease state that may be alleviated at least in part with a combined Th1 and Th2 or Th2-like immune response, the next step may be to determine disease specific antigens. The subsequent step may be to co-administer the disease specific antigens with P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof, and at least one adjuvant known to induce a Th1 immune response, to induce a combined Th1/Th2 immune response. Co-administration of disease specific antigens, adjuvants for a Th1 immune response, and adjuvants of the present invention that elicit a Th2 or Th2-like immune response can be sequentially or concurrently delivered intravenously, intra-arterially, intra-muscularly, intra-dermally, intra-tumorally, or orally. Any pharmaceutical carrier or diluent that maintains the solubility of the components can be used.

EXAMPLE 12

Using P. gingivalis LPS as a Vaccine Adjuvant

The invention contemplates a method to elicit a Th2 or Th2-like immune response in a subject to prevent disease onset. After identifying a disease state that may be prevented with a Th2 or Th2-like immune response, the next step may be to determine disease specific antigens. The next step may be to co-administer the disease specific antigens with P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, mimetics thereof, or any combination thereof, to induce a Th2 immune response. Co-administration of disease specific antigens and adjuvants of the present invention that elicit a Th2 or Th2-like immune response can be sequentially or concurrently delivered intravenously, intra-arterially, intra-muscularly, intra-dermally, or orally. Any pharmaceutical carrier or diluent that maintains the solubility of the components can be used.

---

---

We claim:

1. A pharmaceutical composition comprising disease-specific antigens and at least one isolated lipid moiety selected from the group consisting of P. gingivalis LPS, detoxified P. gingivalis LPS, derivatives of P. gingivalis LPS, derivatives of detoxified P. gingivalis LPS, P. gingivalis Lipid A, detoxified P. gingivalis Lipid A, derivatives of P. gingivalis Lipid A, derivatives of detoxified P. gingivalis Lipid A, and mimetics thereof.

2. The pharmaceutical composition of claim 1, further comprising a co-adjuvant which elicits a Th1 immune response.

3. A pharmaceutical composition comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof and a co-adjuvant which elicits a Th1 immune response.

4. A method of eliciting a Th2 immune response in a mammal comprising administering to said mammal an adjuvant comprising at least one isolated lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

5. A method of enhancing the immunogenicity of a vaccine in a mammal comprising co-administering to said mammal disease-specific antigens and an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

6. A method of modulating immunocompetence of a mammal comprising administering to said mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

7. A method of enhancing antibody harvest in a laboratory animal through elicited Th2 immune response comprising administering to said animal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof; and harvesting at least one antibody from said animal.

8. A method for treating an autoimmune disease in a mammal comprising administering to said mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

9. A method for treating an infectious disease in a mammal comprising administering to said mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

10. A method of modulating the Th2 immune response in a laboratory animal comprising administering to said mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

11. A method of stimulating IL-5 production in a mammal comprising administering to said mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

12. A method of stimulating IL-13 production in a mammal comprising administering to said mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

13. A method of dampening IFNγ production in a mammal comprising administering to said mammal an adjuvant comprising at least one lipid moiety selected from the group consisting of *P. gingivalis* LPS, detoxified *P. gingivalis* LPS, derivatives of *P. gingivalis* LPS, derivatives of detoxified *P. gingivalis* LPS, *P. gingivalis* Lipid A, detoxified *P. gingivalis* Lipid A, derivatives of *P. gingivalis* Lipid A, derivatives of detoxified *P. gingivalis* Lipid A, and mimetics thereof.

14. The method of claim 4, 6, 7, 8, 9, 10, 11, 12 or 13, further comprising co-administering to said mammal disease-specific antigens.

15. The method of claim 4, 5, 6, 7, 8, 9, 10, 11, 12 or 13, further comprising co-administering to said mammal a co-adjuvant which elicits a Th1 immune response.

16. The method of claim 14, wherein said adjuvant and said disease-specific antigens are administered concurrently.

17. The method of claim 14, wherein said adjuvant and said disease-specific antigens are administered sequentially.

18. The method of claim 14, further comprising co-administering to said mammal a co-adjuvant which elicits a Th1 immune response.

19. The method of claim 18, wherein said adjuvant, said disease-specific antigens and said co-adjuvant are administered concurrently.

20. The method of claim 18, wherein said adjuvant, said disease-specific antigens and said co-adjuvant are administered sequentially.

21. The method of claim 15, wherein said adjuvant and said co-adjuvant are administered concurrently.

22. The method of claim 15, wherein said adjuvant and said co-adjuvant are administered sequentially.

* * * * *